US008420025B2

(12) United States Patent  
Potyrailo et al.

(10) Patent No.: US 8,420,025 B2
(45) Date of Patent: Apr. 16, 2013

(54) METHODS AND SYSTEMS FOR DELIVERY OF FLUIDIC SAMPLES TO SENSOR ARRAYS

(75) Inventors: Radislav A. Potyrailo, Niskayuna, NY (US); Prashant V. Shrikhande, Trevose, PA (US); Scott M. Boyette, New Hope, PA (US); Caibin Xiao, Harleysville, PA (US); Andrew M. Leach, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 2 days.

(21) Appl. No.: 13/359,023

(22) Filed: Jan. 26, 2012

(65) Prior Publication Data

US 2012/0121466 A1    May 17, 2012

Related U.S. Application Data

(60) Division of application No. 11/507,689, filed on Aug. 22, 2006, now Pat. No. 8,133,741, which is a continuation-in-part of application No. 11/259,643, filed on Oct. 26, 2005, now Pat. No. 7,723,120.

(51) Int. Cl.
| | |
|---|---|
| *B01L 3/00* | (2006.01) |
| *G01N 15/06* | (2006.01) |
| *G01N 21/00* | (2006.01) |
| *C12M 1/00* | (2006.01) |
| *C12M 1/34* | (2006.01) |

(52) U.S. Cl.
USPC ....... 422/502; 422/68.1; 422/82.05; 422/400; 422/500; 436/95; 436/164; 436/174; 436/180; 435/286.4; 435/287.1; 435/287.2

(58) Field of Classification Search .................. None
See application file for complete search history.

(56) References Cited

U.S. PATENT DOCUMENTS

| 3,744,975 A | 7/1973 | Mailen |
| 4,323,536 A | 4/1982 | Columbus |

(Continued)

FOREIGN PATENT DOCUMENTS

| DE | 102004013161 A1 | 10/2005 |
| EP | 0 902 394 A1 | 9/1997 |

(Continued)

OTHER PUBLICATIONS

Barnard et al., "Fiber-Optic Organic Vapor Sensor", Environ. Sci. Technol., 25, No. 7, pp. 1301-1304, 1991.

(Continued)

*Primary Examiner* — Neil N Turk
(74) *Attorney, Agent, or Firm* — Wegman Hessler & Vanderburg

(57) ABSTRACT

Total analysis systems and methods for simultaneously monitoring a suite of biological and/or chemical species in water and/or other process systems are disclosed. The system provides a sample-volume controlled sensor array comprising a fluid delivery device and a plurality of optical sensor elements for determining the presence and total concentrations of multiple analytes in the process system simultaneously. Delivery means are provided to deliver a metered quantity of sample fluid to the sensor array. Image identification algorithms are provided for identifying the analytes based on image intensity, color pattern, positional arrangement, and the like. The methods incorporate multivariate optimization algorithms to analyze multiple sensor responses. This produces analytical results that are typically difficult to obtain without full system or variable compensation. The improved array response may then be utilized to measure, monitor, and control the concentration of analytes in the chemical or biological sample or water system.

10 Claims, 24 Drawing Sheets

U.S. PATENT DOCUMENTS

| | | | |
|---|---|---|---|
| 4,756,884 | A | 7/1988 | Hillman et al. |
| 4,857,453 | A | 8/1989 | Ullman et al. |
| 4,877,586 | A | 10/1989 | Devaney, Jr. et al. |
| 5,132,345 | A | 7/1992 | Harris et al. |
| 5,164,598 | A | 11/1992 | Hillman et al. |
| 5,234,813 | A | 8/1993 | McGeehan et al. |
| 5,290,705 | A | 3/1994 | Davis |
| 5,300,779 | A | 4/1994 | Hillman et al. |
| 5,354,692 | A | 10/1994 | Yang et al. |
| 5,478,751 | A | 12/1995 | Oosta et al. |
| 5,492,840 | A | 2/1996 | Malmqvist et al. |
| 5,599,913 | A | 2/1997 | Harris et al. |
| 5,885,527 | A | 3/1999 | Buechler |
| 5,941,821 | A | 8/1999 | Chou |
| 6,001,307 | A | 12/1999 | Naka et al. |
| 6,011,882 | A | 1/2000 | Dasgupta et al. |
| 6,030,581 | A | 2/2000 | Virtanen |
| 6,113,855 | A | 9/2000 | Buechler |
| 6,295,506 | B1 | 9/2001 | Heinonen et al. |
| 6,341,182 | B1 | 1/2002 | Fitzgerald et al. |
| 6,360,585 | B1 | 3/2002 | Potyrailo et al. |
| 6,379,969 | B1 | 4/2002 | Mauze et al. |
| 6,514,199 | B1 | 2/2003 | Alessandri |
| 6,591,124 | B2 | 7/2003 | Sherman et al. |
| 6,604,050 | B2 | 8/2003 | Trippel et al. |
| 6,641,533 | B2 | 11/2003 | Causey, III et al. |
| 6,645,142 | B2 | 11/2003 | Braig et al. |
| 6,648,820 | B1 | 11/2003 | Sarel |
| 6,676,903 | B2 | 1/2004 | Potyrailo et al. |
| 6,908,593 | B1 | 6/2005 | Shartle |
| 7,022,286 | B2 | 4/2006 | Lemke et al. |
| 7,083,920 | B2 * | 8/2006 | Werner et al. ............. 435/6.12 |
| 7,393,502 | B2 | 7/2008 | Okubo et al. |
| 7,473,397 | B2 | 1/2009 | Griffin et al. |
| 7,476,361 | B2 * | 1/2009 | Kellogg et al. ............. 422/72 |
| 7,723,120 | B2 | 5/2010 | Xiao et al. |
| 2002/0015994 | A1 | 2/2002 | Schellenberger et al. |
| 2002/0040208 | A1 | 4/2002 | Flaherty et al. |
| 2002/0052050 | A1 | 5/2002 | Douglas et al. |
| 2002/0189374 | A1 | 12/2002 | DeSilets et al. |
| 2002/0192811 | A1 | 12/2002 | Pitt et al. |
| 2002/0195463 | A1 | 12/2002 | Seki et al. |
| 2003/0005964 | A1 | 1/2003 | Lechner-Fish et al. |
| 2003/0032071 | A1 | 2/2003 | Wang et al. |
| 2003/0157586 | A1 | 8/2003 | Bonde et al. |
| 2004/0028566 | A1 | 2/2004 | Ko et al. |
| 2004/0057873 | A1 | 3/2004 | Yerazunis et al. |
| 2004/0191924 | A1 | 9/2004 | Hunter et al. |
| 2004/0206399 | A1 | 10/2004 | Heller et al. |
| 2004/0265172 | A1 | 12/2004 | Pugia et al. |
| 2005/0111328 | A1 | 5/2005 | Potyrailo et al. |
| 2005/0112358 | A1 | 5/2005 | Potyrailo et al. |
| 2005/0176059 | A1 | 8/2005 | Pal et al. |

FOREIGN PATENT DOCUMENTS

| | | | |
|---|---|---|---|
| EP | 1548423 | A | 6/2005 |
| JP | 11161775 | A | 6/1999 |
| JP | 2004028775 | A | 1/2004 |
| JP | 2005233974 | A | 9/2005 |
| WO | WO 95/11961 | A1 | 5/1995 |
| WO | WO 96/15576 | A1 | 5/1996 |
| WO | WO 97/40181 | A1 | 10/1997 |
| WO | WO 99/21655 | A1 | 5/1999 |
| WO | WO 99/58245 | A1 | 11/1999 |
| WO | WO 01/07889 | A2 | 2/2001 |
| WO | WO 01/94921 | A2 | 12/2001 |
| WO | WO 02/43864 | A2 | 6/2002 |
| WO | WO 02/071929 | A2 | 9/2002 |

OTHER PUBLICATIONS

Yang et al., "Chemcial Sensing Using Sol-Gel Derived Planar Waveguides and Indicator Phases", Anal. Chem. 67, No. 8, pp. 1307-1314, Apr. 15, 1995.

Van De Merbel et al., "Sampling and Analytical Strategies in On-Line Bioprocess Monitoring and Control", Journal of Chromatography A, 725, pp. 13-27 1996.

Jackman et al., "Fabricating Large Arrays of Microwells with Arbitrary Dimensions and Filling Them Using Discontinuous Dewetting", Anal. Chem., vol. 70, No. 11, pp. 2280-2287, Jun. 1, 1998.

Potyrailo et al., "Adapting Selected Nucleic Acid Ligands (Aptamers) to Biosensors", Anal. Chem. vol. 70, No. 16, pp. 3419-3425, 1998.

Potyrailo et al., "Optical Waveguide Sensors in Analytical Chemistry: Today's Instrumentation, Apps, and Trends for Future Development", Fresenius J Anal. Chem., 362, pp. 349-373, 1998.

Delamarche et al., "Microfluidic Networks for Chemical Patterning of Substrates: Design and Application to Bioassays", J. Am. Chem. Soc., 120, No. 3, pp. 500-508, 1998.

Bakker et al., "Ion Sensors: Current Limits and New Trends", Analytica Chimica Acta, 393, pp. 11-18, 1999.

Ghauch et al., "Quantitative Measurements of Ammonium, Hydrogenophosphate and Cu(II) by Diffuse Reflectance Spectrometry", Talanta, 48, pp. 385-392, 1999.

Michael et al., "A Far-Field-Viewing Sensor for Making Analytical Measurements in Remote Locations", Anal. Chem., vol. 71, No. 14, pp. 2766-2773, 1999.

Byrne, et al., "Digital Imaging as a Detector for Generic Analytical Measurements", Trends in Analytical Chemistry vol. 19, No. 8, pp. 517-522, 2000.

Hirayama et al., "Visual and Colorimetric Lithium Ion Sensing Based on Digital Color Analysis", Anal. Chem., vol. 72, No. 3, pp. 465-474, Feb. 1, 2000.

Dickson et al., "Integrated Chemical Sensors Based on Carbon Black and Polymer Films Using Standard CMOS Process and Post-Processing", Proceedings of IEEE International Symposium, pp. 341-344, May 2000.

Albert et al., "Cross-Reactive Chemical Sensor Arrays", Chem. Rev., 100, pp. 2595-2626, Jun. 24, 2000.

Rakow et al., "A Colorimetric Sensor Array for Odour Visualization", Nature, vol. 406, pp. 710-713, Aug. 17, 2000.

Cunningham, "Fluidic and Sample Handling in Clinical Chemical Analysis", Analytica Chimica Acta, 429, pp. 1-18, 2001.

Byrne et al., "Digital Imaging as a Detector for Quantitative Colorimetric Analyses", Proceedings of SPIE, 4205, pp. 267-277, 2001.

Sequeira et al., "Towards Autonomous Environmental Monitoring Systems", Talanta, 56, pp. 355-363, 2002.

Polerecky et al.,"Optimization of Absorption-Based Optical Chemical Sensors that Employ a Single-Reflection Configuration", Applied Optics, vol. 41, No. 15, pp. 2879-2887, May 20, 2002.

Suzuki et al, "Ionophore-Based Lithium Ion Film Optode Realizing Muliple Color Variations Utilizing Digital Color Analysis", Anal Chem, vol. 74, No. 22, pp. 5766-5773, Nov. 15, 2002.

Juncker et al., "Autonomous Microfluidic Capillary System", Anal. Chem., vol. 74, No. 24, pp. 6139-6144, 2002.

Kompany-Zareh et al. "Simple Method for Colorimetric Spot-Test Quantitative Analysis of Fe(III) Using Computer Controlled Hand-Scanner", Anal Chimica Acta, 471, pp. 97-104, 2002.

Stevens et al., "Imaging and Analysis of Immobilized Particle Arrays", Analytical Chemistry, vol. 75, No. 5, pp. 1147-1154, Mar. 1, 2003.

Manzano et al., "Computer Screen Illumination for the Characterization of Colormetric Assays", Sensors and Actuators B, 96, pp. 173-179, 2003.

Bowden et al., "The Determination of Phosphorus in a Microfluidic Manifold Demonstrating Long-Term Reagent Lifetime and Chemical Stability Utilising a Colorimetric Method", Sensors and Actuators B, 90, pp. 170-174, 2003.

Lau et al., "Solid State Ammonia Sensor Based on Berthelot's Reaction", Sensors and Actuators B, 98, pp. 12-17, 2004.

Lau et al., Novel Fused-LEDs Devices as Optical Sensors for Colorimetric Analysis, Talanta, 63, pp. 167-173, 2004.

Zhang et al., "A Colorimetric Sensor Array for Organics in Water", J. Am. Chem. Soc.,vol. 127, pp. 11548-11549, 2005.

Freitag, "Sampling Modules, in Biosensors in Analytical Biotechnology", Academic Press, Inc., pp. 1-21, 1996.

Carr-Brion et al., "Sampling Systems for Process Analyzers", Butterworth-Heinemann, Oxford, England, 1996.
Zolotov et al., Chemical Test Methods of Analysis, Wilson & Wilson's Comprehensive Analytical Chemistry, Elsevier, 2002.
International Search Report mailed Jul. 4, 2007 for PCT/US2006/041352 filed Oct. 23, 2006.
International Preliminary Report on Patenability issued Apr. 29, 2008 for PCT/US2006/041352 filed Oct. 23, 2006.
Preliminary Rejection issued in corresponding Korean Patent Application No. 2008-7012576 dated Oct. 30, 2012.

* cited by examiner

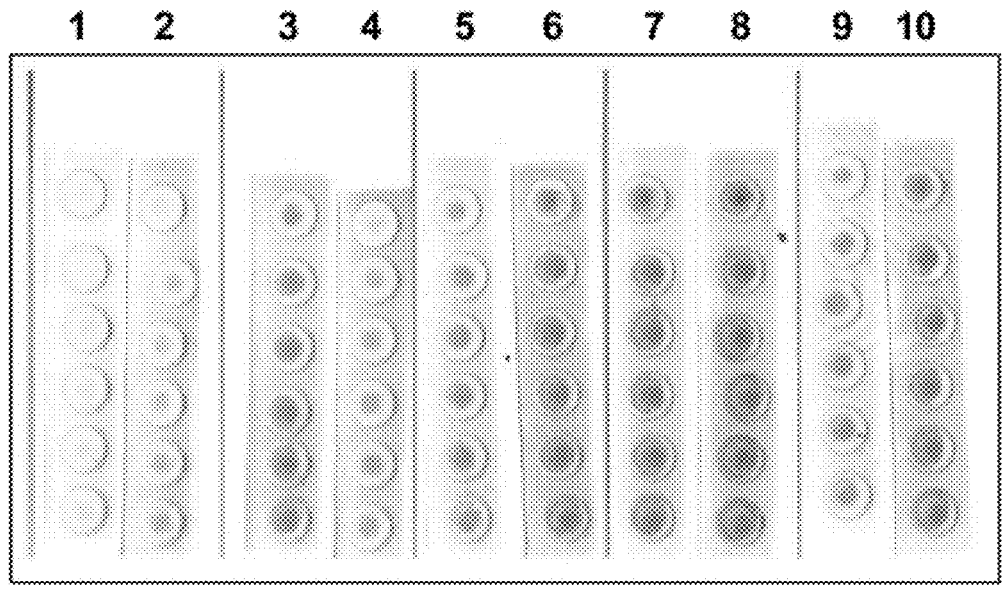
Fig. 7
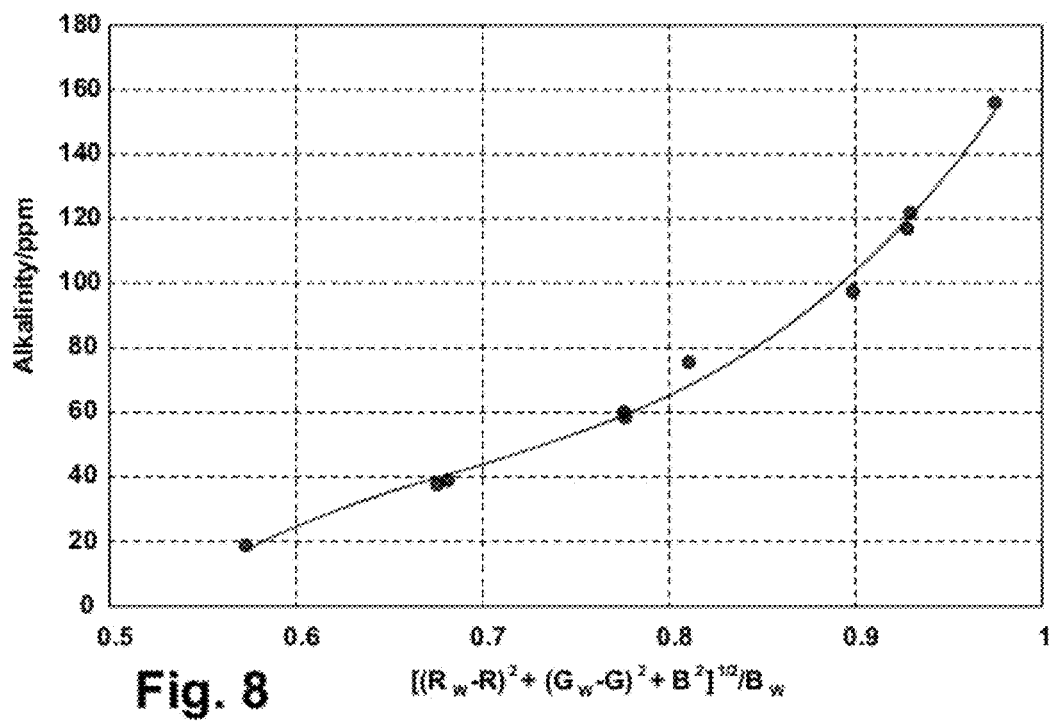
Fig. 8  $[(R_w-R)^2 + (G_w-G)^2 + B^2]^{1/2}/B_w$

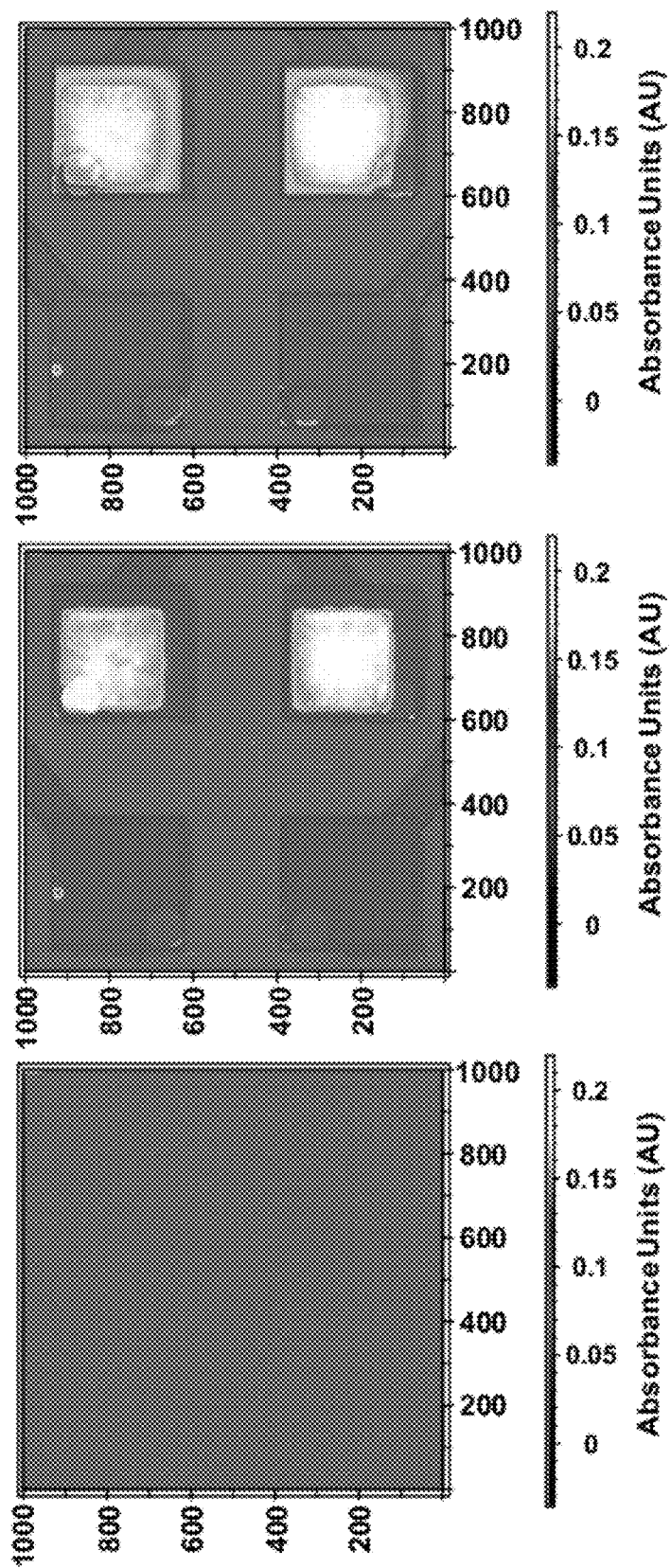

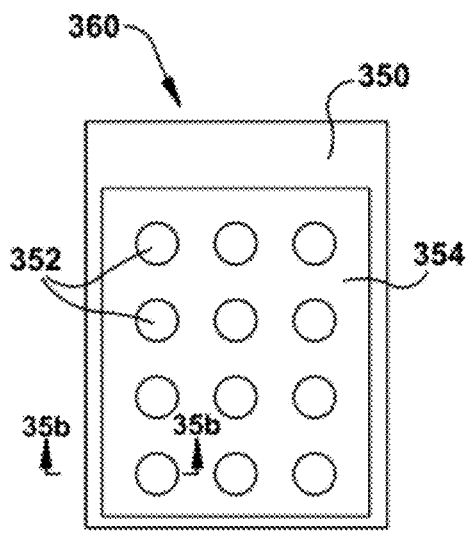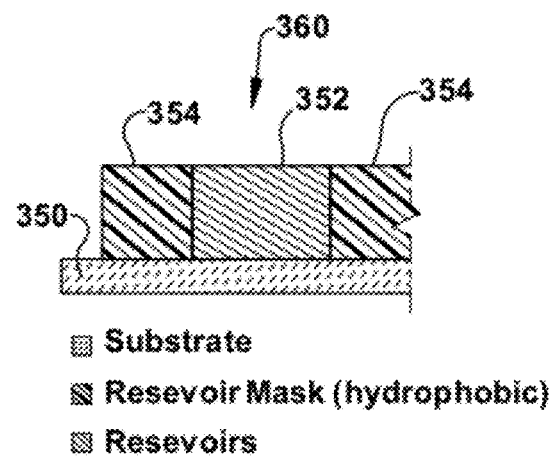
Fig. 34a
Fig. 34b
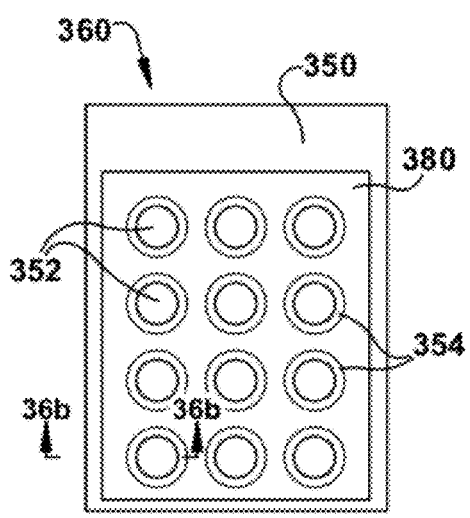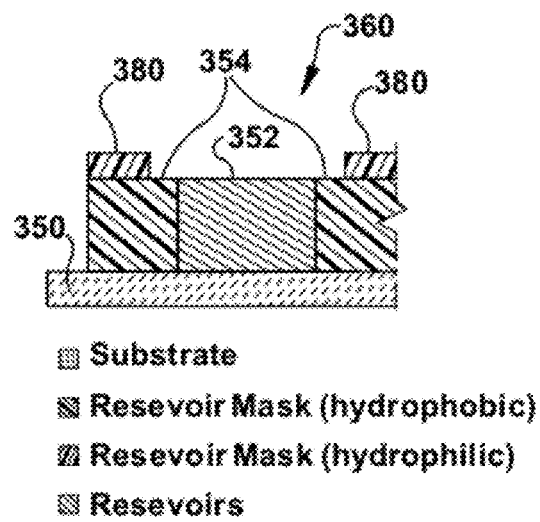
Fig. 35a
Fig. 35b

METHODS AND SYSTEMS FOR DELIVERY OF FLUIDIC SAMPLES TO SENSOR ARRAYS

CROSS REFERENCE TO RELATED APPLICATION

This application is a divisional of U.S. patent application Ser. No. 11/507,689, filed Aug. 22, 2006, which is a continuation-in-part of U.S. patent application Ser. No. 11/259,643 filed Oct. 26, 2005, now U.S. Pat. No. 7,723,120.

FIELD OF INVENTION

The present invention relates generally to a chemical sensor array, and more particularly relates to a new and improved system, method and apparatus for delivering a fluid sample to a chemical sensor array, and parallel processing chemical and biochemical information from a multiplicity of sensor elements of the sensor array.

BACKGROUND OF THE INVENTION

Many chemical and biological measurements need to be performed in locations outside of a fully equipped analytical facility. This requires systems that are portable and miniaturized so that they can be transported to locations where rapid test response is required for process or water quality monitoring, or they can be deployed in a medical environment to provide rapid test results for certain biological or biochemical species of interest. These chemical and biological analyses can be performed individually using single tests with post-test optimization to enhance the quality or accuracy of the results, but this serial approach has inherent flaws because multidimensional interactions are difficult to fully compensate using a serial approach. Additionally, this approach can be time consuming and can produce erroneous results. Introducing operator or system errors when tests are performed on different platforms or at different times further complicates this system. The best way to overcome this limitation is to perform all the desired measurements simultaneously on the same platform, but current state of the art does not provide a fully integrated platform for such measurements.

Current electrochemical array technology allows operators to perform an arrayed test at a single time, but this is limited to those materials that respond to an electrochemical stimulus. This usually involves measurement techniques like anodic stripping voltametry or cyclic voltametry methods, or incorporates chemically responsive material into an electrochemical detector, e.g., an ion-specific electrode (ISE). This system, although productive for some systems is limited by many of the common limitations of electrochemical systems, e.g., systematic problems at low and high ionic strength that effect electrochemical potentials. Additionally, some of these systems can suffer from serious cross-reactivities or interferences, e.g., the cross-reactivity of common oxyanions or small cations like sodium, lithium, and potassium.

There are other test platforms that could provide small-scale array measurements that are based on optical or spectral measurements. These can be optical detection from multi-flow wet chemical analysis, or they can be portable versions of classic laboratory measures, e.g., portable atomic absorption spectrometer units. These systems are often limited by mechanics required for fluid flow and maintenance, or from cumbersome equipment like portable atomic absorption spectrometer systems that, although theoretically transportable, have proven less mobile in practice. There is also mention of miniaturizing additional lab systems like Inductively Coupled Plasma—Atomic Emission Spectroscopy or Mass Spectroscopy, but these methods are difficult to adapt into portable handheld, or field deployable systems.

A proposed alternative is to use an optical platform based on well-characterized, chemical responses of optical sensor films Such a system uses solid, chemically responsive films that respond to analyte concentrations by changing their absorbance values at an optimized wavelength. This platform can be extended to incorporate sensor test elements for all known interfering or cross-reactive species for a particular test matrix, as well as account for test limitations at the extremes of the test sample conditions, e.g., high and low ionic strength as well as high and low buffer strengths. This system has the added benefit of providing a small test platform that can be formed into an array specifically designed to measure test elements that require specific deconvolution analysis.

Optical chemical sensors also fall into two general classes, reversible and irreversible. Fully reversible sensors equilibrate rapidly to the concentration of the target analyte in the test fluid and their response changes when the analyte concentration changes. Examples of reversible sensors are polymer film pH sensors and ion selective optodes (ISO). In contrast, an irreversible sensor will continue to respond to the analyte in the test fluid until the responsive reagent in the sensor has been exhausted, i.e., the total amount of analyte available to the sensor rather than the analyte concentration in the sample. Many non-ISO type sensors belong to this category.

Since the reagent in the reversible sensors is at chemical equilibrium with the analyte in the sample, the exposure of the sensor film to the sample alters the analyte concentration if the sample volume is finite. This requires that the reversible sensor films be exposed to either a large excess amount of sample volume or a given amount of sample volume. In the latter case, a correction can be made to reduce errors due to the finite volume effect. Similarly, the irreversible sensor requires sample volume control so that the sensor response reflects the analyte concentration in the controlled volume of the test fluid.

A sensor array designed for quantitative analysis may not yield satisfactory results by just immersing the array element into a liquid sample because the above mention reasons. For a sensor array consisting of both reversible and irreversible sensors, the sample volume that each sensor region is exposed to has to be controlled. Moreover, volume regulation also helps prevent sensor-to-sensor cross contamination. In this invention, sensor film compositions are designed to be at their optimized performance when they are exposed to fixed sample volumes.

Optical sensor arrays that are composed of irreversible sensors, or a combination of irreversible and reversible sensors, must have some form of fluidic control that delivers a controlled volume of test fluid to each sensor element. Most systems available today use some form of pump or mechanical multi-addition system to deliver these controlled volumes, e.g., robotic addition to multi-well plates. These systems are often cumbersome and require mechanical and electrical components that are rarely field robust and suitable for remote testing in harsh environments. Dedicated sampling systems for analytical instruments have been developed that differ in their functionality and capabilities depending on their end use. A variety of sampling approaches are known for sensors, for example, sequential exposure of sensor regions to chemicals of interest as disclosed in our prior U.S. Pat. No. 6,360,585; and sampling from multiple regions over large areas as disclosed in our prior U.S. Pat. No. 6,676,903. The disclosures of both of these patents are hereby incorporated by reference herein.

In recent years, capillary effect has been exploited for fluidic designs. One drawback associated with this passive mechanism is that it relies on the use of absorbent or wicking materials. This makes it difficult to fabricate a device to deliver a small amount of sample to a large number of locations. Instead, the absorbent material is an integrated part of sensing or reaction matrix. Liquid delivered to the site result in only wetting the materials within the matrix. For sensor array applications, dosing a given amount of liquid sample to multiple locations is more desirable.

Even though a large number of publications and patents have been devoted to the development of sensor methods, reagents, and equipment to replace the traditional wet chemistry methods, a need remains for an economical and convenient field deployable sensor system for simultaneous detection of multiple analytes.

What is also needed is an improved method and system for delivering a controlled amount of a liquid sample to multiple sensor regions within a given time period without using any pumps, valves or wicking materials. In many areas of science and technology, it is often required to deliver a given amount of fluidic sample to multiple locations. In determination of analyte concentrations, a fluidic sample needs to be dispensed to multiple detection sites where multiple analytes in the sample can be analyzed. In high throughput screening and combinatorial research, it is desirable to distribute a liquid reactant to an array of reaction sites. Conventionally, liquid delivery to multiple locations is accomplished by means of pumping, liquid-jet dispersing, and methods similar to simple manual or mechanical pipetting such as the liquid dispersing robot system.

In recent years, capillary effect has been exploited for fluidic designs. One of the drawbacks associated with known passive mechanisms is that they typically rely on the use of absorbent or wicking materials. This makes it difficult to fabricate a device to deliver a small amount of sample to a large number of locations. Moreover, devices disclosed in the prior art are not capable of delivering a fluid packet to multiple sensor regions. Instead, the absorbent material is an integrated part of sensing or reaction matrix. Liquid delivered to the site only results in wetting the materials within the matrix. As a result, for many applications dosing a given amount of liquid sample to multiple locations is more desirable.

SUMMARY OF THE INVENTION

In one aspect, the invention is directed to a sample-volume controlled sensor system for simultaneously measuring multiple analyte concentrations in chemical or biological substances such as water systems comprising a set of reversible and irreversible analyte-responsive sensor elements which are selected to change at least one optical property in response to chemical, biological, or environmental stimuli, including at least one reference region that serves as an internal optical and position standard, and a light source for directing light onto an array of sensor elements. A detector-based imaging device is provided which can adjust its performance to the position and spectral profile of the light source, and then converts this imaged response into a digital record. Image identification algorithms are provided to identify the test composition on the element by one of many configurations based on image intensity, color pattern, arrangement, and the like. A software-based optimization algorithm is provided which incorporates responses from the sensor array and produces optimized results unavailable without full system and variable compensation.

In another aspect, the invention is directed to a device comprising channels and reservoirs capable of delivering a controlled amount of a liquid sample to multiple reservoirs containing an array of sensor elements within a given time period. The driving force for liquid transport within the device is mainly capillary force generated by the surface energy of the liquid and channel/reservoir wall interface. Such a device does not rely on the use of any wicking materials and can be produced inexpensively using readily available materials. Other methods for directing fluids to sensor arrays which are considered to be within the scope of the present invention include electro-osmotic flow, electrowetting, thermocapillary pumping, magnetic fields, surface directed flow, electrochemical control, mechanical (e.g. syringes), centripetal, and surface energy gradients. One application of the present invention is to deliver controlled volumes of liquid samples to sensor arrays on optical disks.

Also disclosed is a total analysis method for monitoring a suite of biological and chemical species in water and process systems. The system provides a sample-volume controlled array of reversible and irreversible optical sensors to determine total concentrations of multiple analytes simultaneously. The method involves exposing the sensor array to a multiple analyte-containing media, and recording the sensor array response as a digital record. The sensor response is processed to reduce noise and interference, and multivariate analysis is applied to improve the array response. The improved array response is then utilized to measure, monitor, and control the concentration of analytes in the chemical or biological substance or water system.

BRIEF DESCRIPTION OF THE DRAWINGS

FIG. 7 is an image of alkalinity sensitive films;

FIG. 8 is a graph that illustrates $[(R_w-R)^2+(G_w-G)^2+B^2]^{1/2}/B_w$ calculated from a digital image captured with a scanner plotted a function of solution alkalinity;

FIGS. 32a-32c illustrate dynamic absorbance imaging to evaluate operation kinetics of the assembled sampler with sensor elements that provide controlled leaching of reagents into the controlled sample volume;

FIG. 34a illustrates an exemplary embodiment of the present invention;

FIG. 34b is a partial cross-section view of the exemplary embodiment of FIG. 34a;

FIG. 35a is an exemplary embodiment of the present invention;

FIG. 35b is a partial cross-section view of the exemplary embodiment of FIG. 35a;

DETAILED DESCRIPTION OF EXEMPLARY EMBODIMENTS

Figure 1:
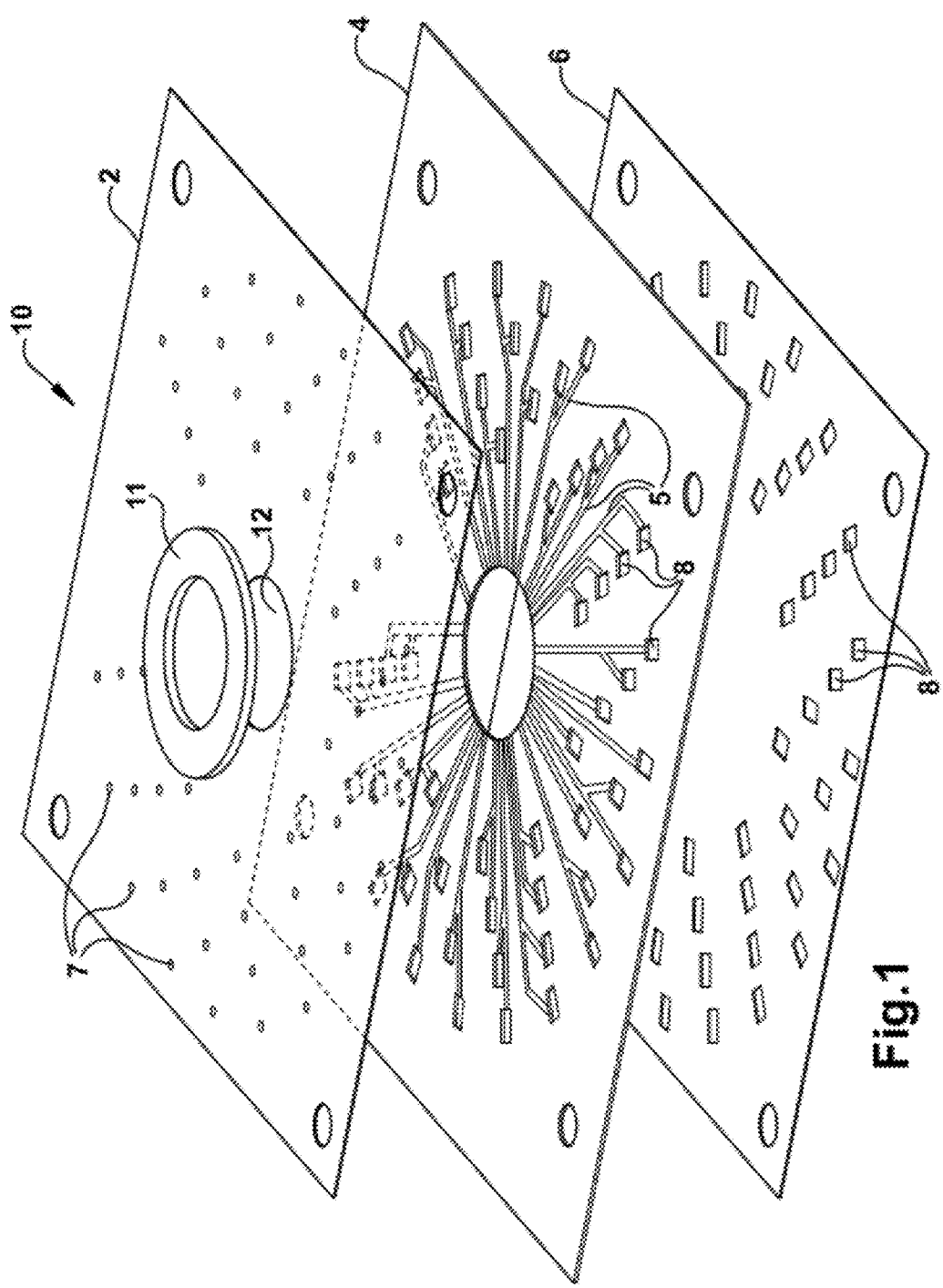
FIG. 1 is a perspective view of an assembly stack for the capillary-flow fluid delivery sampling device in accordance with an exemplary embodiment of the present invention.

This invention describes a test array platform that incorporates noise reduction, interference reduction, improvements from multi-chemistry response, multivariate analysis and a flexible platform, that allows test arrays to be custom designed to provide optimized response with minimized systematic or operator errors. This array-based testing platform is based on chemically responsive optical sensor elements that can be incorporated into rugged, field deployable systems composed of a simple detection array, and these systems can be easily interfaced with computer or electronic units that can perform the complex analysis required to provide optimized measurements at non-laboratory locations.

One aspect of the present invention is the recognition that optical sensor films can be developed to account for most systematic variables that effect chemical and biological analyte measurements. These chemical and biological sensors systems contain several functional components. One component is a sensor material that responds to a change in the environment. Examples of such sensor materials are analyte-responsive polymers, biomembranes, sol-gels, and some others. In the case of optical sensors, the sensor material should maintain adequate optical transparency or loss of transparency for the chemically responsive composite to be monitored using optical transmission, reflection, dispersion, fluorescence, or any other common optical method known in the art. Another component described herein is the electronic system that provides means of measuring the change in the sensor material upon environmental exposure. Accordingly, interactions of the environment with the material are converted into an analytically useful signal using an appropriate transduction mechanism such as optical sensing. This arrayed optical detection platform is interfaced with a "smart system" that compensates for interferences, environmental variations, etc., and performs noise reduction and test optimizations and produces final results of greater quality than can be obtained with a system that is not as fully integrated.

The following sections describe in more detail the components of this total analysis system, with examples of how each component can provide increased improvement when applied to a complete array test platform. The total analysis system is a product of combining each of these improved elements to produce a single system with enhanced performance that results from the simultaneous combination of the individual elements.

Sensor Array

An optical sensor array has a set of analyte-responsive elements where the sensor elements respond to analyte concentrations by changing color or other optical properties upon exposure to a sample. The number of total sensor elements and the type of sensor elements can be selected to meet a specific system analysis need. As a non-limiting example, one sensor array for water analysis comprises optical sensor elements responding to the following analytes: Alkalinity, pH, chlorine, hardness, sulfite, and phosphate.

Suitable sensor types for use in the present invention are described in our co-pending patent applications entitled "Material Compositions for Sensors for Determination of Chemical Species at Trace Concentrations and Method of Using Sensors" and "Self-Contained Phosphate Sensors and Method for Using Same" filed on the same date as the present application, the disclosures of which are hereby incorporated by reference herein.

Optical sensor arrays comprise an array of solid sensor elements deposited on a solid substrate. The solid element can contain a single or multiple components. One or all components in the solid sensor element could be water-soluble. Combinations of different solubility characteristics of the components in the sensor element can be chosen to enhance sensor array performance. As an example, the sensor element can be prepared from a hydrogel polymer containing water soluble reagents that respond to analyte concentration.

A binder may be used to enhance adhesion of the solid element to the substrate. A liquid spreading material, e.g., a surfactant, may be added to the solid element to improve the wetting properties of the sensor regions. The liquid spreading material may be placed in between the solid element and the substrate, or in other configurations such as on the top of or surrounding the element. Commonly practiced methods that are suitable to prepare the sensor array needed for this invention include the methods for manufacturing indicator paper strips and polymer film sensors as described by Zolotov et al. in "Chemical Test Methods of Analysis" in *Wilson & Wilson's Comprehensive Analytical Chemistry*, 2002, the disclosure of which is hereby incorporated by reference herein.

Array Light Source—Detector Combinations

There are many light source/detector combinations suitable to measure sensor responses on an optical array. For example, our prior U.S. patent application Ser. No. 10/760,438 filed Jan. 20, 2004 describes a handheld device with a disposable element for chemical analysis of multiple analytes, the disclosure of which is also hereby incorporated by reference herein.

Turning to our present invention, the invention pertains to novel systems and methods for simultaneously detecting parallel film responses from a plurality of sensor elements. The table below shows sources for UV-visible-near -IR ranges for the applications in conjunction with optical sensor array system, and for parallel processing of chemical and biochemical information suitable for use in the present invention. It is understood that other less conventional light sources that emit radiation in the spectral range of interest such as sun, organic light emitting diodes, indoor room lights, products of bioluminescence reaction, emission of electronic equipment such as computer monitors, PDA monitors, displays of cell phones, pagers, radioluminescent sources, and any other light sources known or later developed in the art could also be used without departing from the scope of the present invention.

Light Sources Useful For Optical Sensors

| Source | Spectral range of emission (nm) |
|---|---|
| Continuous wave sources: | |
| Xenon arc lamp | 200-1000 |
| Mercury arc lamp | 250-600 |
| Deuterium lamp | 180-420 |
| Tungsten lamp | 320-2500 |
| Light emitting diodes | different diodes cover range from about 250 to 1500 nm |
| Diode lasers | different diode lasers cover range from about 400 to 1500 nm |
| Argon ion laser | several lines over 350-514 nm |
| Helium-neon laser | several lines over 543-633 nm |
| Krypton laser | several lines over 530-676 nm |
| Pulsed sources: | |
| Nitrogen laser | 337 nm |
| Nd: YAG laser | fundamental - 1064, frequency doubled - 532, tripled - 355 |
| Ti: Sapphire laser | 720-1000, frequency doubled 360-500 |
| Dye lasers | 360-990 frequency doubled 235 to 345 |

Possible detectors include vacuum or solid state and single or multichannel detectors. Vacuum detectors are phototubes and photomultiplier tubes (PMT). Solid-state detectors include photodiodes, photodiode arrays, charge-coupled devices (CCDs), charge-injection devices (CIDs), and avalanche photodiodes. Multichannel detectors include arrays of individual detectors such as photodiode arrays, PMT arrays. Also, CCDs, CIDs, CMOS, and other types of multichannel detectors are available. Each element has its intrinsic advantages and disadvantages and can be combined to produce a light source detector platform suited to the particular need in a specific application. Similarly, it is possible to combine more than one light source or detector to monitor different types of responses on sensor films, and then combine them into a common array platform in a manner known in the art.

As an example, a color image of a subject can be recorded by illuminating with any of the cited or envisioned light sources and captured by a digital scanner or camera. A CCD color sensor in the digital camera measures the intensities of the three primary colors (red, green, and blue) of the subject. The Red-Green-Blue (RGB) color intensity value of each pixel is recorded in a digital file. The color depth, or the range of RGB values, is usually 0 to 255. Colors can also be measured by the CCD color sensor in a digital scanner using a white light source for illumination and some form of simple color light detector. Some digital scanners, however, use three LEDs (red, green, and blue) to irradiate the subject for the color measurement. Unlike digital cameras, most digital scanners provide a 48-bit, or greater, color resolution. In this color model, the color of each pixel is quantified by RGB values in the range of 0 to 65025. The spectral ranges of the three primary colors measured by the digital camera and scanner vary slightly from model to model. The spectral response of a typical CCD color sensor is 460±40 nm, 540±40 nm, and 645+/−55 nm, respectively. We use a digital imaging device for quantitative colorimetric analysis. In this aspect, the digital imaging device is equivalent to multiple, three-color LED/photodiode pairs.

Fluidic Delivery System

FIG. 1 illustrates a fluidic delivery device 10 in accordance with an exemplary embodiment of the present invention. The delivery device 10 transports a controlled amount of a liquid sample, in metered quantities, to multiple reservoirs 8 in order to effect a chemical reaction between the sample fluid and the sensor elements (not shown) connected to the reservoirs 8. As shown in FIG. 1, the fluid delivery device 10 comprises a top cover layer 2, a middle channel layer 4, a bottom sampler-substrate binding (i.e., gasket) layer 6, a fluid entry port 12, and an associated plastic entry port wall ring 11. A plurality of grooves or channels 5 are formed on the channel layer 4 for directing the sample fluid from the fluid entry port 12 to the reservoirs 8. A plurality of channels is formed when the cover layer 2 is bound to the channel layer 4. A series of vent holes 7 are added to assure complete fluid flow through the channel system.

Many commercially available hydrophilic films can be chosen as the top layer to fabricate the device disclosed in this invention. Some films have a heat sealable adhesive deposited on the hydrophilic side. For those films without adhesives, standard-bonding methods can be used to laminate the cover layer to the channel layer such as ultrasonic welding and adhesive transfer bonding. Hydrophilic films may be both heat sealable and pressure sensitive adhesive.

The channel layer 4 can be fabricated using conventional plastic processing methods such as injection molding, hot embossing, and micro machining Many plastic materials that have water contact angle in the range of 40 to 85 degree can be used for the channel layer. For example, polycarbonate and acrylic are suitable materials for this application.

The sampler binding layer 6 can be any material that has durometer number around 40 Shore A and provides seal to a flat substrate by surface wetting, conformal contact and/or adhesive bonding. Non-limiting exemplary materials for this application are silicone and synthetic rubbers, and thermoplastic elastomers. The sampler binding layer 6 could be an extruded silicone sheet. A double side adhesive material could also be used. The sampler binding layer 6 can be bonded to the channel layer using adhesives, although by choosing a high-heat plastic material, such as polycarbonate or Ultem, insert or two-part molding of the sampler binding material to the channel layer can be done.

The cover layer 2 provides a super hydrophilic surface for the fluidic channel, which contributes largely to the overall capillary force that drives the fluid to flow through the channel The cover layer also accommodates a plurality of small holes 7, one over each reservoir 8, to allow for the passage of air, which is displaced out from the reservoir by the incoming liquid. Due to the capillary force driving the fluid through the channels 5, no pumps and valves are required to deliver a given amount of liquid sample or reagent from the sample entry port 12 to the multiple reservoirs 8 within a predefined sequence. As a result, the device 10 can be efficiently fabricated by inexpensive plastic processing methods. The fluid delivery device 10 may then be integrated as a component of a chemical or biological sensor array system to transport and dose, in metered quantities, a sample liquid into the reservoirs 8 in order to complete a reaction with the associated sensor elements.

In order to effectively fill a reservoir 8 from a channel 5 that has a smaller capillary dimension than the reservoir itself is not a trivial matter. The transition zone from the channels to the reservoir is likely to act like a capillary barrier in obstructing the passage of liquid from the end of the channel to the reservoir. An external force, such as gravitational force, may be needed to overcome this barrier. In other cases, channel and reservoir parameters are carefully balanced to shorten the transition time and yet avoid overflow through the vent holes 7.

The present invention overcomes the capillary barrier transition problem described above by implementing the following design features. First, a one-sided super hydrophilic film is chosen for the cover layer, which enables the liquid to advantageously accumulate over the entire top wall of the reservoir to form a pendant droplet. As the droplet grows, gravitational force enables it to reach the bottom wall of the reservoir and then capillary force originated from the four walls of the reservoir drives the liquid to fill the entire reservoir. As the reservoir completely fills, the vent hole serves as a capillary barrier, impeding the liquid from flowing through it to reach the top surface of the cover layer, which is designed to be hydrophobic. Secondly, we adjust the fluid flow resistance through optimization of channel and reservoir geometric parameters, hydrostatic pressure from the entry port, and capillary pressure of the channel in order to achieve a desirable fill volume and filling sequence. In addition, the sampler binding layer 6, which appears as part of the sidewalls of the reservoir 8, creates a capillary barrier as the pendant drop grows. Therefore, a careful design of the channel and reservoir parameters, including the sampler binding thickness, is important to overcome this barrier to ensure complete filling of each reservoir.

Referring again to FIG. 1, each channel 5 can feed single or multiple reservoirs 8. If a channel is required to feed multiple reservoirs due to space consideration, a simple branched-type structure as shown in FIG. 1 may be constructed to help prevent trapping of air bubbles in the channel 5. In the branched-type configuration, the filling sequence of reservoirs can be easily controlled based on their relative overall flow resistance. If the channel dimensions are the same within the structure, the reservoir filling sequence depends on the length of the channel connecting the reservoir and the entry port.

Figure 2:
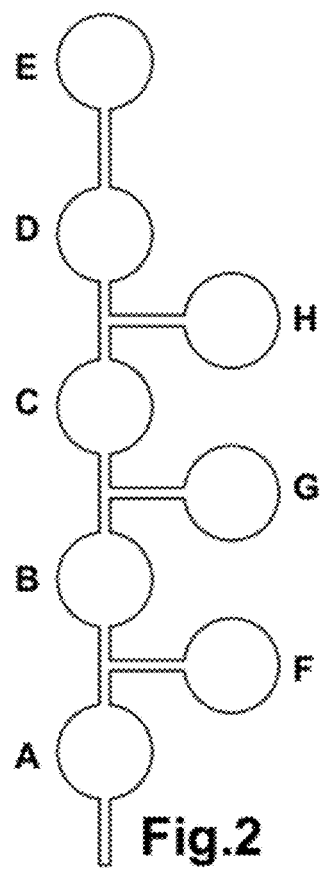
FIG. 2 illustrates a branched series channel-reservoir configuration in accordance with another exemplary embodiment of the present invention.

FIG. 2 illustrates another exemplary embodiment in which the reservoirs 8 are connected in series or branched-series configuration. This configuration is useful for applications in which it is desired to add a reagent at different dosages to the sample stream before it reaches different branched reservoirs in the branched-type configuration. For example, if an acidic reagent soluble to the sample stream immobilized in reservoirs A, B, C, and D, liquids in reservoirs E, F, G, and H will contain a different amount of acid. The configuration shown in FIG. 2 makes it possible to study a reaction between the liquid sample with a reagent in branched reservoirs F, G, and H under different pH conditions. This type of fluidic manipulation is usually very difficult to achieve with conventional methods based on pumps and valves.

Figure 3:
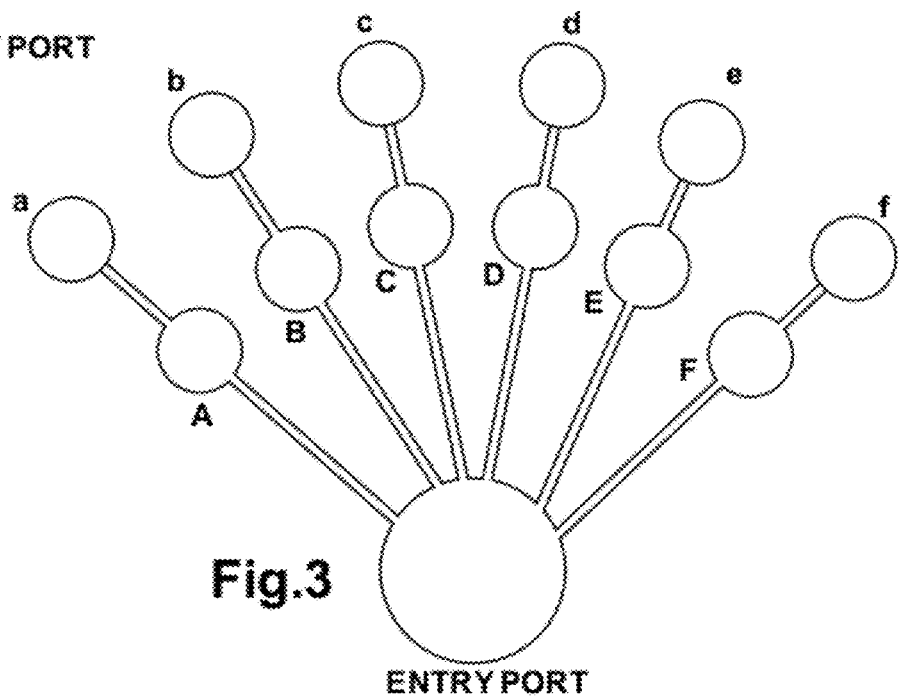
FIG. 3 illustrates a parallel-series channel-reservoir configuration in accordance with another exemplary embodiment of the present invention.

FIG. 3 shows a parallel series configuration. With this configuration, one can immobilize different soluble reagents in reservoirs A, B, C, D, E, and F, and the same reagent in reservoirs a to d. Thus, one can create an array of sensor reactions between the liquid sample with a reagent in reservoirs a, b, c, d, and f in the presence of reagents delivered through reservoirs A, B, C, D, and F.

Reservoirs A to D shown in FIG. 3 can be used to cover the sensor elements while reservoirs a to d is used for sample volume control. By changing the volume of reservoirs a to d, one can control the effective sample delivered to reservoirs A to D.

In a similar fashion to the process described in FIGS. 2 and 3, reservoirs A, B, C, D, E could contain a material or membrane that removes a species or chemical from the liquid flowing in the channels, thus modifying the liquid or removing interferences prior to the liquids arrival at subsequent reservoirs.

Figure 4:
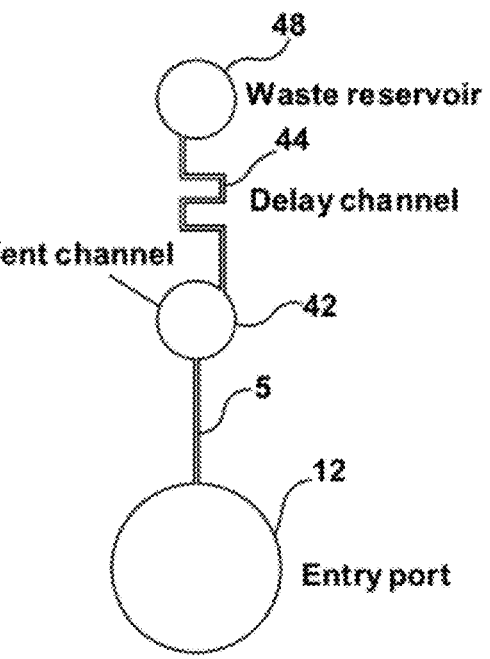
FIG. 4 illustrates a fluid delivery configuration with a waste reservoir and a delay channel in accordance with another exemplary embodiment of the present invention.

FIG. 4 shows a configuration that allows first filling the reaction reservoir 42 with a first liquid sample for a short period, and then withdrawing the first liquid sample to a waste reservoir 48. After the first liquid is withdrawn to the waste reservoir, a second liquid sample can be added to the entry port, and driven to fill the reaction reservoir. In order to achieve these fluidic functions, capillary pressure generated by the waste reservoir 48 should be greater than that by the reaction reservoir 42 and the channel 5 connecting between the reaction reservoir 42 and the entry port 12. The delay time can be controlled by varying the length or/and flow resistance of the delay line 44.

Another important but optional feature of the fluidic delivery device 10 disclosed in this invention is that it is removable from a substrate. The substrate provides the bottom wall of the reservoir, and the sampler binding layer provides a liquid seal to the substrate. This is especially advantageous comparing to many fluidic devices disclosed in the prior art when sensor or reaction elements have to be included in the reservoir. Using this liquid delivery device, the substrate can be prepared independently.

Since the device disclosed in this invention can be separated from the substrate after its use, it can be a reusable device, although it is also suitable to being treated as a disposable component. Also, the substrate can be reusable if analyte-responsive sensor are reversible or regeneratable.

Reference materials can be used to normalize the sensor response. This can be any stable material whose spectrometric properties are not affected by the environmental or system parameters experienced by the array, e.g., temperature, light, and humidity. Alternatively, they could be the substrate itself whereupon sensor elements are deposited, or these reference materials could be incorporated into the films, affixed to array structure, or be the array material of construction. These materials can be any spectral standard from black to white, of any applicable wavelength suitable to the particular array system design. The reference materials could also be dyes, organic, or inorganic pigments that have spectral bands that do not significantly overlap with spectral bands of the sensor element. The reference material may also comprise an optical response material such as inorganic, organic, and polymeric photonic crystals.

Normalization using the response from the internal references is useful for reduction of errors caused by variation in the optical path length, dimensions of the sensor element, and other variation sources known in the art. More specifically, including an internal reference in the sensor element is important in two situations. First, if the sensor element before exposure is transparently colorless, optical measurements before exposure to the sample may not provide any useful information for sensor response normalization. Secondly, if a measurement on the sensor element cannot be carried out before its exposure to the sample, reading at the $\lambda_{max}$ (maximum wavelength) of the internal reference after the exposure can be used to correct the sensor response at the $\lambda_{max}$ of the sensor element. Since the internal reference is an integrated part of the sensor element, tracking changes in its optical response provides information on the physical state of the sensor element after its exposure to the sample and environment. For example, changes in the physical state of the sensor element due to swelling or loss of transparency contribute to the overall sensor response. Differences in signal readings at the $\lambda_{max}$ of the internal reference before and after the exposure can be used to separate the sensor response due to analyte-sensor interaction from that due to changes in the sensor physical state.

Multiple reference materials can also be deposited on the sensor array and RGB values measured from the reference areas can be used to normalize the sensor response and eliminate any variation that may be caused by illumination changes during the image capture process. The normalization can reduce array-to-array variations introduced in the manufacturing, storage, or sample application processes.

Secondary effects can limit the performance of an array detection system. These effects include noise from the array sensor system, effects from environmental or system parameters, defects caused during the manufacturing or sample application processes, as well as unexplained outliers in the data set, such as interferences, that alter the true analyte response. Minimizing secondary effects can be accomplished by using an individual reduction tool or by combining more than one tool, if appropriate.

Noise reduction can be used to improve array response using several categories of data manipulation. In one envisioned form of noise reduction a digital image file is generated and stored in a computer or microprocessor, and noise reduction methods are applied to analyze the raw data. These can include, but are not limited to, Fourier transforms, wavelet transform, Kalman filtering, Savitsky-Golay smoothing, running mean, median, and polynomial methods. In the case of color response, RGB values over each sensor region can also be averaged. In another instance, selective data elimination can be applied where one calculates standard deviations within a smaller area centered at each pixel inside the sensor element, referred to as subset standard deviation. If the subset standard deviation of a group of pixels is greater than a pre-set value, this group of pixels can be rejected from the set.

In another envisioned form of secondary effect reduction, the system can have elements that sense environmental variables such as temperature, where the temperature measure can be used to account for predetermined variations due to this or similar environmental measures. Similarly, additional measurement elements can be included to account for general system parameters such as sample clarity, system conductivity, oxidation reduction potential, or similar variables that can affect array response. Having measures of these additional variables allows the system to compensate for effects not fully compensated using simpler analytical tools.

In another envisioned form of secondary effect reduction, a system can be established to eliminate response from defective solid sensor film defects. Some defects are caused by out of spec formulations that are used to prepare the sensor films that result in spatial inhomogeneities of the films, or might be introduced into the film preparation steps, such as inclusion of dust particles in the film. Foreign materials might also be deposited on the film during the exposure to the sample matrix. A digital image provides very high spatial resolution on color intensity distribution over each sensor region. This spatial information can be exploited for noise reduction. A variety of data analysis tools can be used to reduce errors from film defects, and an algorithm may be applied to discriminate noises caused by the defects. For example, averages and standard deviations of the RGB values for the whole area of the sensor element are first calculated. We refer to them as set averages and standard deviations, respectively. Then the RGB values from each pixel are compared with the set averages. If the difference is greater than a pre-set multiple of the set deviation, this pixel can be rejected from the set. A similar calculation can be used to reject a group of pixels. Defects in the sensor elements may also exhibit unique color or/and spatial patterns, such as lines and dots. Pattern recognition algorithm may be applied to identify the defect regions. Additionally, defects in the sensor elements are not normally distributed. The optical response from the defect regions is either greater or less than the set average. Thus, normality test can also be used to reject readings from the defects. This is especially useful when the overall sensor film quality is poor and a significant amount of white noise exists in the set.

Interacting system contaminants can also cause errors in array results. Compensation for interferences can be made if the concentration of the interfering species can be measured directly, or if it can be inferred from parallel response from dissimilar sensor films The interdependent nature of chemical species in solution could result from interferences, where these interferences can be caused by competing reactions of interfering species with the sensing reagent. The traditional wisdom has been focused on the development of interference free chemical reagents for an individual analyte. Chemometric data analysis algorithms have been used to analyze overlapping spectral response for interference reduction, and this has been described in the literature.

A three-part data generation and analysis method is used in this invention to solve interference problems. First, we design sensors to measure parameters that define the chemical and physical state of the sample. These parameters include temperature, pH, and alkalinity. Second, we design sensors that respond independently to a group of interference species. Third, we design sensor films that respond to the same analyte, but that have dissimilar interference response. The sensor responses from these sensors are deconvoluted to review true concentration for each analyte among the interference species. One can also compare the response pattern of the sensor suite from the measured sample to the stored model. The stored model is built from the responses of the sensor films to a range of analyte species and their combinations with the additional responses of the sensor films to expected interferences at their different levels. By capturing different sensor response at various combinations of analytes and interferences, the model captures the response pattern over the analytes dynamic range of interest. The tools for quantitative analysis of sensor films in their combination include neural network, principal components regression, locally weighted regression, partial least squares and any others known in the art.

Multivariate analysis has been widely used in analytical chemistry, especially in spectroscopic analysis. One aspect of the present invention is that a systematic method is utilized to simultaneously determine multiple analyte concentrations in a water or process sample. An exemplary method disclosed in this invention provides a sensor array comprising multiple sensor elements that are chosen to de-convolute the interdependent nature of the chemical equilibrium in water or process systems. The sensor array provided may include sensor elements that are specifically designed to be responsive to water or process parameters that are needed for multivariate analysis, and that would otherwise not be needed as part of a simple, but less accurate analysis. Additionally, the array platform allows systems with multi-response chemistries to be used, and that are interpreted by deconvoluting the dual response results.

Determination of pH, alkalinity, hardness, and phosphate are non-limiting examples of the complex nature of a water system testing, where different analytes produce interdependent responses. pH is by definition a measure of hydrogen ion activity that is defined by thermodynamic properties of the water sample. pH is also affected by carbonate concentrations in the same water sample, and carbonate exists in several aqueous forms whose proportions are determined by a complex series of equilibria as defined by the system pH. Carbonate and corresponding phosphate equilibria provide buffering environments. Buffer is a mixture of a conjugate acid-base pair that can resist changes in pH when small amounts of strong acids or bases are added. The buffer capacity of a solution is the number of moles of strong acid or strong base needed to change the pH of 1 Liter of buffer solution by 1 pH unit. Hardness is referred to as the total calcium and magnesium concentration, including numerous forms of calcium and magnesium species that may exist in the system. Some of these calcium and magnesium forms may include phosphates, and these phosphate salts are in equilibrium with soluble forms of the contributing ions. The ion concentrations exist in a complex equilibrium that balances the pH with carbonate, phosphate, and hardness concentrations. Phosphate can also exist in additional forms in water, and again, the respective phosphate forms are determined by a pH, alkalinity, and counterion balance in a series of interrelated equilibria. One can use a phosphate optode to measure phosphate, but a phosphate optode may respond to just one ionic form of phosphate in water, e.g., mono-hydrogen phosphate ions ($HPO_4^{2-}$) species. In order to obtain the total phosphate concentration, the sample pH, carbonate, and hardness concentrations must also be known. All the species in the water system are in chemical equilibrium, and all the contributing equilibria must be accounted for when determining a single analyte concentration. One must measure all these analyte concentrations as well as account for environmental properties like temperature to make an accurate measure of the single analyte.

The mathematical details of this complex chemical and thermodynamic equlibria are well known in the art and will not be described in detail in the present disclosure, but a simpler example based on alkalinity and pH will give an exemplary account of the difficulties associated with multi-equlibria measurements made with solid film sensor that use color responsive reagents. The purpose of this non-limiting example is to illustrate one of the systematic methods disclosed in this invention.

pH is defined by equation below:

$$pH = -\log 10\ a_{H^+},\ (\text{where } a_{H^+} \text{ is activity of hydrogen ion}).$$

Hydrogen ion is related to other chemical species in the system through the following equilibrium:

$$H_2O(l) \Leftrightarrow H^+(aq) + OH^-(aq),$$

$$HA(aq) \Leftrightarrow H^+(aq) + A^-(aq).$$

HA(aq) stands for a aqueous Bronsted acid, and $A^-$ is the conjugate base of HA(aq). The existence of Bronsted acids and bases give rise not only to acidity or basicity of the system but also to pH buffer capacity. The pH buffer capacity is usually measured as alkalinity in the water treatment industry, and this is primarily a function of the total carbonate concentration.

When a sample is applied to a pH sensor region, a pH sensing reagent such as a pH indicator dye, referred to as "Ind" hereafter, interacts with the hydrogen ion in the sample through equilibrium below:

$$Ind + H^+(aq) \Leftrightarrow IndH^+.$$

The change in the indicator concentration according to above equilibrium is used to determine the pH value of the sample. The indicator molecules (Ind and $IndH^+$) have different spectrum, and a change in spectral absorbance indicates a shift in equilibrium, which can reflect shifts in system pH, and the change of the indicator concentration is usually measured by a change in the optical properties of the sensor region. The optical properties include absorbance and fluorescence.

Since the pH indicator itself is usually a Bronsted acid or base, as indicated in the above equilibrium, the pH measuring process perturbs the acid-base equilibrium in the sample, which results in a measurement error for pH. The numerical value of this error is a function of the buffer capacity of the system. Therefore, one has to know alkalinity of the system to determine pH accurately.

A sensor array for pH and alkalinity analysis comprises multiple sensor elements. Some elements measure sample alkalinity, while other elements measure sample pH, and the combination of these multiple sensor elements are used to extend the detection range for the array. The response of the sensor element to alkalinity can be made independent of the sample pH, and the alkalinity of the sample can be obtained from just alkalinity elements. As mention above, the response of the pH sensor elements is a function of both pH and alkalinity. A two-dimensional calibration surface can be obtained for pH and alkalinity. The pH value of the sample can be determined using the measured alkalinity value and interpreting the sensor response using the two-dimensional calibration surface.

Kinetic Response

Often, for quantification, a sensor response should reach a steady state upon exposure to the sample. In practice, some sensors have a long response time and it takes an unacceptably long time to reach steady state, and measuring the sensor response at any single time may result in errors due to variations in timing. For a sensor array, different response reading methods should be applied. For non-steady state sensors, time-dependent measurements are required. Kinetic information can be interpreted for the dynamic characteristics of the system such as the initial slope, slope at a given time, and intercepts of a selected segment of the response curve.

Additionally, temporal response can also provide a sensitive measure of both analyte response as well as reflect the presence or concentration of contaminants that effect the sensor response kinetics. Similarly, the kinetic response can be used to measure the concentration of catalyzing agents that may be in the system, making the temporal response independent of the sensor array equilibrium measure. Many time series statistic models can be used to treat the non-steady state sensor response. In general, the final reading and the responses prior to the final reading can be fitted into a model to minimize the instrumental and measurement errors.

Total Analysis System

As described herein, the total analysis system of the present invention includes an optical array platform comprising diverse chemically or physically responsive sensor films The system produces an optical response proportional to the desired chemical or physical parameter, provides secondary effect reduction from noise, defect, and interference effects, compensates for multivariate interactions, accounts for test array history, and provides a reference system to calibrate the sensor array response to the optical detection platform. This complex test array can be combined with time-based data acquisition to provide temporal test analysis that can further enhance overall array response. The complex array elements described herein show how each element enhances the array performance, and how the combination of these elements produces optimized environmental and biological measurements. Further, this enhanced optical array platform is advantageously suited for non-laboratory environments.

In other aspects of the invention, internal reference materials are included as an integrated part of the sensor array. The reference materials allow normalization of sensor response to eliminate variations caused by variation in illumination, sensor element quality, and environmental parameters. In addition, the present invention provides solutions to specific problems associated with the digital imaging techniques known in the art.

In other aspects of the invention, the sample volume that each sensor element is exposed to is controlled by a capillary-flow-based fluidic device which transports and doses, in metered quantities, a controlled volume of sample liquid to the sensor elements. In this way, the fluid delivery device of the present invention makes it possible to efficiently construct a sensor array with both reversible and irreversible sensor elements.

The following examples are included to demonstrate the broad applicability of the present invention. It should be appreciated by those of skill in the art that the techniques disclosed in the examples which follow represent techniques discovered by the inventors, and thus can be considered to constitute exemplary modes for its practice. However, those of skill in the art should, in light of the present disclosure, appreciate that many changes can be made in the specific embodiments which are disclosed and still obtain a like or similar result without departing from the scope of the invention.

EXAMPLE 1

Figure 20:
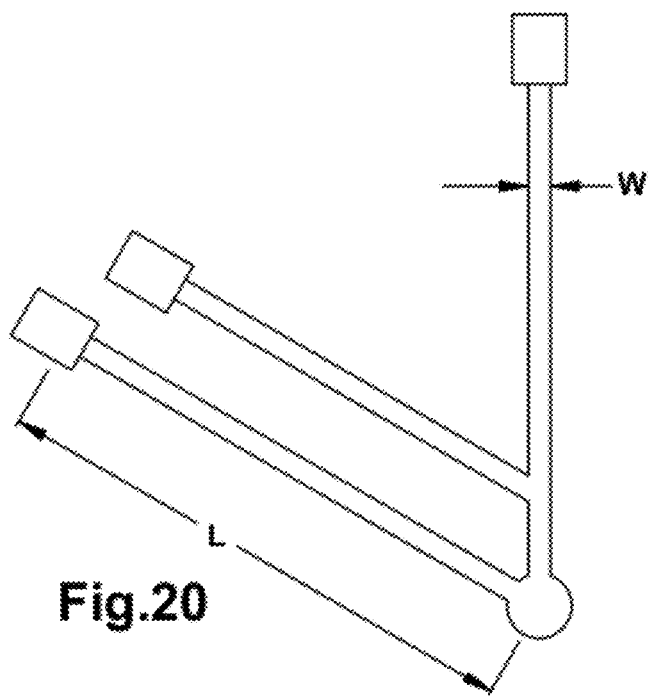
FIG. 20 shows the channel and reservoir layout for Example 1.
Figure 21:
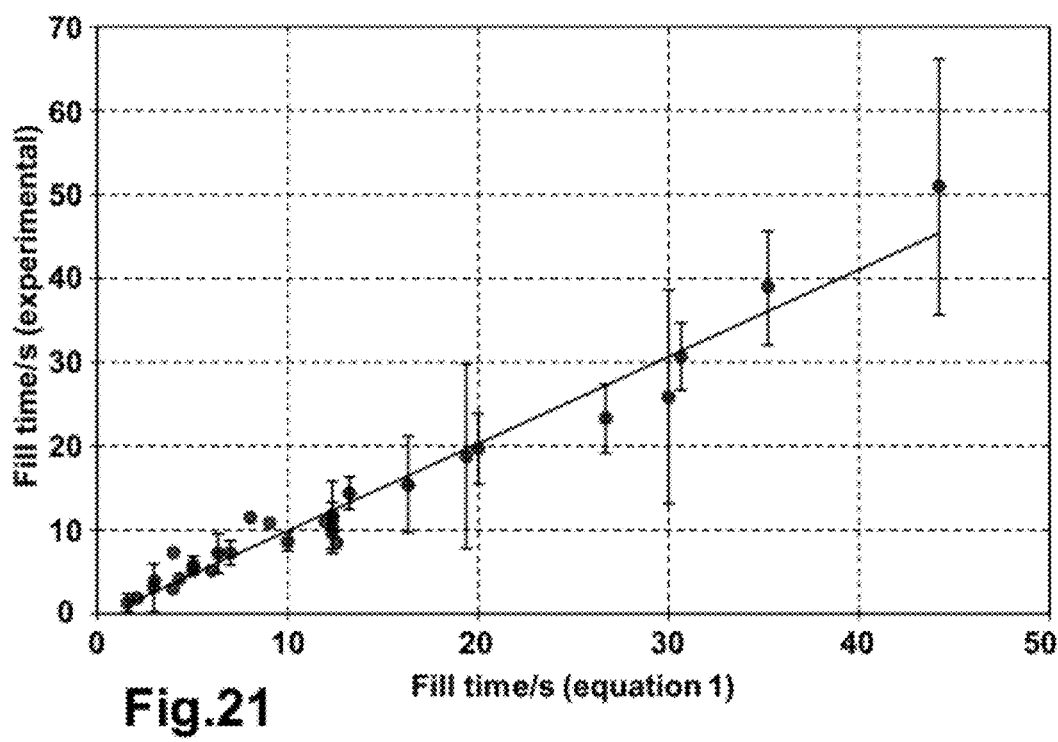
FIG. 21 shows comparison of predicted fill time with experimental fill time data for Example 1.

Reservoir fill time as a function of channel and reservoir geometric parameters. The channel and reservoir layout are shown in FIG. 20. The device comprises three layers as shown similarly in FIG. 1. The top cover layer 2 is a heat sealable hydrophilic film. Vent holes 7 (1.5 mm diameter) were cut through this layer. The middle channel layer 4 is a 0.78 mm thick polycarbonate sheet with open channels 5 and rectangle openings (i.e., reservoirs) 8 cut by means of computer numerical controlled (CNC) machining The bottom sampler binding layer 6 is a 40 Shore A silicone gasket, providing seal to a substrate. Rectangle openings are die cut through the gasket. When these layers are laminated to form a fluid delivery device, channels are created between the top hydrophilic layer 2 and middle channel layer 4. The rectangle openings of the channel layer and sampler binding layer define an open-bottom reservoir, with the hydrophilic layer as its top wall. When this assembly is attached to a substrate, closed reservoirs are formed and connected to a central sample entry port through channel Channel and reservoir parameters tested in this example are listed below in Table 1. It was found that reservoir fill time (t/seconds) can be expressed a function below:

$$\mathrm{Log}(t) = K - 0.97251\, \mathrm{Log}(W) - 2.43118\, \mathrm{Log}(D) + 1.346301\, \mathrm{log}(L) + 1.70630 * \mathrm{Log}(D_{gasket}) \qquad \text{Equation (1)}$$

where L, W, and D are channel length, width, and depth, respectively; $D_{gasket}$ is the gasket thickness. Constant K equals $-1.9944$ for single channel to single reservoir configuration, and $-1.7740$ for single channel to two reservoirs configuration. FIG. 21 shows the comparison of fill time predicted by the equation above with experimental data.

TABLE 1

Ranges of channel and reservoir parameters studies in Example 1.

| W/mm | D/mm | L/mm | Gasket/mm | Reservoir per channel |
|---|---|---|---|---|
| 1 | 0.2 | 45 | 0.47 | 1, 2 |
| 1 | 0.3 | 45 | 0.47 | 1, 2 |
| 2 | 0.2 | 45 | 0.47 | 1, 2 |
| 2 | 0.3 | 45 | 0.47 | 1, 2 |
| 1 | 0.2 | 45 | 0.55 | 1, 2 |
| 1 | 0.3 | 45 | 0.55 | 1, 2 |
| 2 | 0.2 | 45 | 0.55 | 1, 2 |
| 2 | 0.3 | 45 | 0.55 | 1, 2 |
| 1 | 0.2 | 12 | 0.55 | 1, 2 |
| 1 | 0.3 | 12 | 0.55 | 1, 2 |
| 2 | 0.25 | 12 | 0.55 | 1 |
| 2 | 0.25 | 21 | 0.55 | 1 |
| 2 | 0.25 | 30 | 0.55 | 1 |
| 2 | 0.25 | 38.5 | 0.55 | 1 |

Reservoir depth = Gasket + 0.78 mm
Reservoir length = 6.0 mm
Reservoir width = 5.0 mm Based on this equation, one can design a device to allow all the reservoirs being filled in a narrow time range although the distance of a reservoir to the central entry port varies. If it is desirable, reservoirs can be filled sequentially by choosing channel parameters according to the equation above.

EXAMPLE 2

Figure 22:
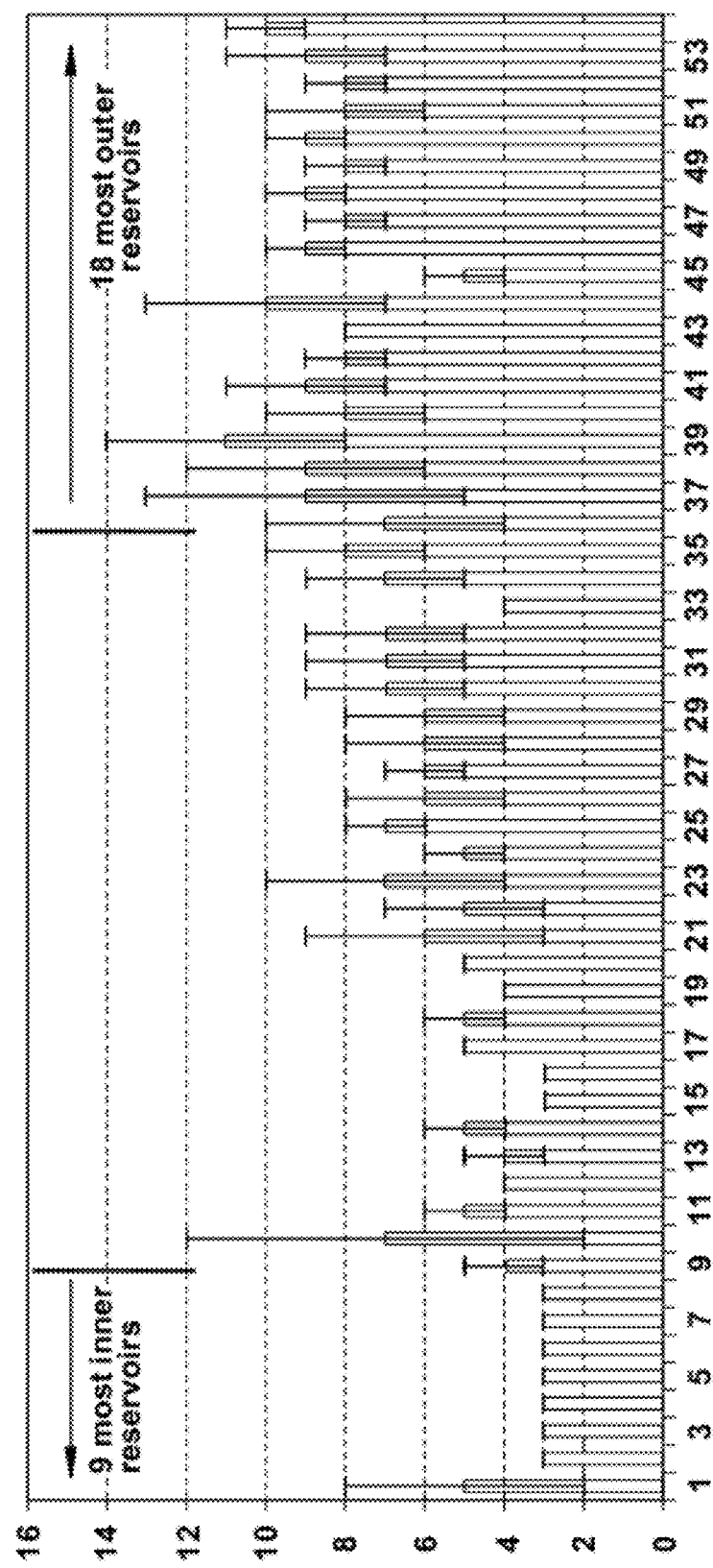
FIG. 22 is a graph that shows average fill time for 54 23 µl reservoirs with error bars obtained from six tests in Example 2.

A 54-reservoir sample delivery device is shown in FIG. 1. The device 10 is assembled from four components by a method similar to that described in Example 1. The channel 5 depth and width are 0.33 mm and 1.5 mm, respectively. The length and width of reservoirs 8 are 5.5 and 4 mm, respectively. The sampler binding layer 6 is cut from a 0.55 mm thick, adhesive backed, and transparent silicone rubber sheet. The thickness of the polycarbonate channel layer 4 is 0.78 mm. Selection of these design parameters was guided by the equation shown in Example 1. A 2.7 ml sample solution containing 100 ppm Basic Blue was delivered to the sample entry port. Real time flow in the channels and reservoirs were monitored using a digital video camera. Fill time for each reservoir was retrieved from the recorded video films Average fill times for all 54 reservoirs obtained from six devices are presented in FIG. 22. The data demonstrate that the device allows delivering a liquid sample to multiple reservoirs in a narrow time range.

EXAMPLE 3

Determination of Chlorine Concentration in a Water Sample

Figure 5:
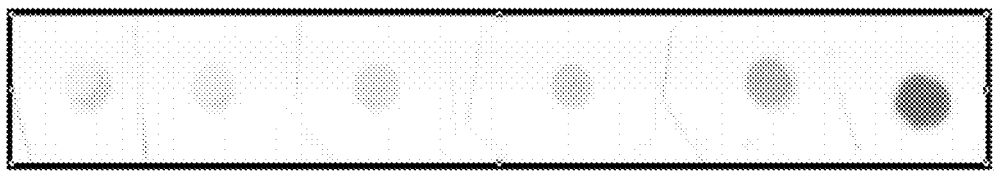
FIG. 5 is an image of chlorine sensitive films from right to left, chlorine concentrations are 1, 2, 4, 5, 10, and 50 ppm.

Six chlorine sensitive films were deposited on a thin translucent polyethylene sheet. A 20 µl chlorine standard solution, prepared from a 5% NaOCl by dilution with deionized water, was spotted on each film. The water sample was removed from the films 1 minute after spotting. A blue color was developed as chlorine in the water sample reacts with the chlorine sensitive reagent immobilized in the films The image of these six films was captured with Hewlett Packard scanner ScanJet 6300C and is shown in FIG. 5. The digital file produced from the scanner was in the JPEG format (67 KB). The color depth was 255. The pixel resolution is 200 dpi.

The digital image was processed with Adobe Photoshop® 6. The film areas were selected using the selection tools provided by the Photoshop software package. Average RGB values for each selected color area are listed in Table 2 below. RGB values for the white paper area of the image, referred to as $R_w$, $G_w$, and $B_w$, are also listed in Table 2.

Figure 6:
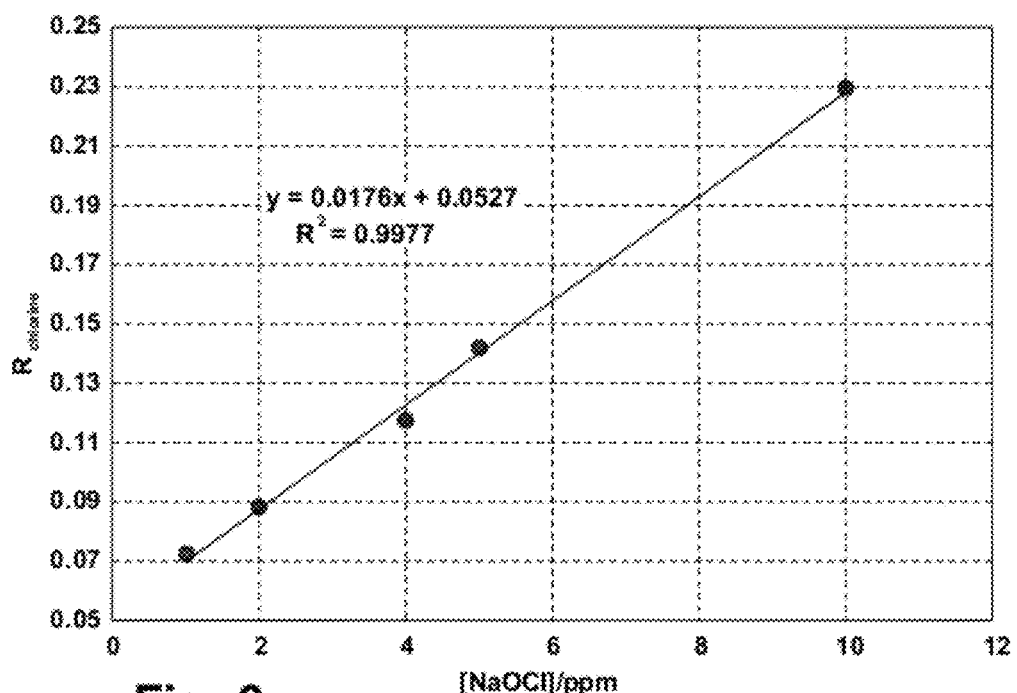
FIG. 6 illustrates the calibration curve for chlorine determination.

As shown in FIG. 6, the quantity defined in Equation 2 below can be used to quantify chlorine concentration.

$$R_{chlorine} = -\log(R/R_w) - \log(G/G_w) - \log(B/B_w) \quad \text{Equation (2)}$$

TABLE 2

Color analysis of chlorine sensitive films shown in FIG. 5

| Chlorine/ppm | R | G | B | $\log(R_w/R) + \log(G_w/G) + \log(B_w/B)$ |
|---|---|---|---|---|
| 1 | 233.63 | 242.67 | 246.35 | 0.0724 |
| 2 | 228.52 | 243.90 | 241.61 | 0.0883 |
| 4 | 219.94 | 242.00 | 236.37 | 0.1178 |
| 5 | 211.46 | 238.44 | 235.95 | 0.1421 |
| 10 | 184.87 | 228.44 | 230.34 | 0.2295 |
| 50 | 124.76 | 199.12 | 190.77 | 0.5418 |
| White paper background | 254.56 | 254.60 | 254.62 | 0.000 |

EXAMPLE 4

Determination of Alkalinity with Multiple Sensor Regions

Six alkalinity sensitive films were deposited on a glass slide. Suitable sensor types used for this example are described in our co-pending patent applications entitled "Material Compositions for Sensors for Determination of Chemical Species at Trace Concentrations and Method of Using Sensors" and "Self-Contained Phosphate Sensors and Method for Using Same" filed on the same date as the present application, and will not be repeated herein. Unlike chlorine analysis, multiple films were used for determination of alkalinity of a single water sample. A 20 µl alkalinity standard solution was spotted on each of the six films The water sample was removed from the films 2 minutes after spotting. Ten alkalinity solutions were measured.

As shown in FIG. 7, the image of total 60 exposed films was captured with Hewlett Packard scanner ScanJet 6300C. The digital file produced from the scanner was in the JPEG format (48 KB). The color depth was 255. Absorbance of the each exposed film at 650 nm was measured with an Ocean Optics USB2000 spectrophotometer.

Average RGB values for the selected color areas are listed below in Table 3. RGB values of the white paper background are 239.41, 239.34, and 244.19, respectively. The following quantity $R_{alk}$ is used to quantify alkalinity:

$$R_{alk} = [(R_w-R)^2 + (G_w-G)^2 + B^2]^{1/2}/B_w. \quad \text{Equation (3)}$$

TABLE 3

Color analysis of films shown in FIG. 7

| Alkalinity/ppm | Film number | R | G | B | R(alk) |
|---|---|---|---|---|---|
| 18.8 [a] | 1 | 227.44 | 227.46 | 137.72 | 0.5682 |
| | 2 | 226.92 | 226.73 | 140.2 | 0.578725 |
| | 3 | 221.63 | 225.69 | 135.09 | 0.560781 |
| | 4 | 221.69 | 225.33 | 135.85 | 0.563968 |
| | 5 | 219.89 | 224.98 | 136.94 | 0.569506 |
| | 6 | 216.71 | 225.18 | 143.37 | 0.59726 |
| | | | | Average | 0.573073 |
| 37.7 [a] | 1 | 221.76 | 225.26 | 139.83 | 0.580045 |
| | 2 | 194.52 | 218.29 | 168.23 | 0.718228 |
| | 3 | 202.97 | 220.22 | 152.49 | 0.646812 |
| | 4 | 195.72 | 219.17 | 165.31 | 0.705072 |
| | 5 | 187.68 | 215.39 | 157.51 | 0.685975 |
| | 6 | 179.48 | 214.16 | 162.75 | 0.717686 |
| | | | | Average | 0.675636 |
| 75.5 [a] | 1 | 180.09 | 212.77 | 157.7 | 0.698513 |
| | 2 | 170.68 | 211.28 | 175.25 | 0.779415 |
| | 3 | 159.29 | 206.99 | 178.37 | 0.811646 |
| | 4 | 152.1 | 204.67 | 185.54 | 0.851659 |
| | 5 | 149.23 | 203.04 | 186.75 | 0.862184 |
| | 6 | 152.45 | 203.97 | 187.63 | 0.859187 |
| | | | | Average | 0.810434 |
| 39.0 [b] | 1 | 210.27 | 220.64 | 132.93 | 0.562534 |
| | 2 | 192.88 | 216.61 | 150.25 | 0.65082 |
| | 3 | 189.62 | 216.16 | 159.76 | 0.691825 |
| | 4 | 182.28 | 213.28 | 153.93 | 0.680802 |
| | 5 | 176.07 | 212.64 | 169.23 | 0.748012 |
| | 6 | 183.77 | 214.95 | 173.86 | 0.754201 |
| | | | | Average | 0.681366 |
| 58.5 [b] | 1 | 187.5 | 215.83 | 154.64 | 0.674907 |
| | 2 | 176.74 | 213.27 | 178.27 | 0.781173 |
| | 3 | 174.38 | 212.25 | 172.24 | 0.762069 |
| | 4 | 167.33 | 210.12 | 176.22 | 0.788816 |
| | 5 | 164.12 | 208.65 | 178.48 | 0.803171 |
| | 6 | 171 | 210.72 | 193.42 | 0.848307 |
| | | | | Average | 0.776407 |

TABLE 3-continued

Color analysis of films shown in FIG. 7

| Alkalinity/ppm | Film number | R | G | B | R(alk) |
|---|---|---|---|---|---|
| 97.5 [b] | 1 | 158.03 | 206.39 | 193.39 | 0.86976 |
| | 2 | 150.32 | 203.24 | 188.28 | 0.865716 |
| | 3 | 138.93 | 198.84 | 189.03 | 0.892229 |
| | 4 | 139.27 | 198.77 | 192.7 | 0.90472 |
| | 5 | 135.26 | 196.68 | 194.44 | 0.920039 |
| | 6 | 133 | 195.89 | 198.3 | 0.938624 |
| | | | | Average | 0.898515 |
| 117.0 [b] | 1 | 142.43 | 200.58 | 197.08 | 0.913398 |
| | 2 | 139.2 | 198.84 | 193.74 | 0.908514 |
| | 3 | 133.99 | 196.92 | 198.26 | 0.935815 |
| | 4 | 132.53 | 195.84 | 195.89 | 0.931041 |
| | 5 | 131.33 | 195.88 | 199.17 | 0.9449 |
| | 6 | 132.71 | 196.04 | 196.04 | 0.931068 |
| | | | | Average | 0.927456 |
| 156.0 [b] | 1 | 132.22 | 195.53 | 197.5 | 0.937564 |
| | 2 | 127.95 | 193.56 | 202.14 | 0.963713 |
| | 3 | 123.56 | 191.45 | 200.69 | 0.969018 |
| | 4 | 110.08 | 189.51 | 205.3 | 1.014391 |
| | 5 | 119.48 | 189.62 | 202.06 | 0.983554 |
| | 6 | 124.03 | 192.11 | 203.77 | 0.97827 |
| | | | | Average | 0.974418 |
| 60.0 [c] | 1 | 187.97 | 215.12 | 143.39 | 0.631684 |
| | 2 | 168.96 | 209.56 | 165.01 | 0.744808 |
| | 3 | 160 | 207.17 | 168.27 | 0.773279 |
| | 4 | 159.19 | 207.64 | 180.98 | 0.821017 |
| | 5 | 155.67 | 206.24 | 178.99 | 0.820522 |
| | 6 | 158.72 | 208.13 | 192.23 | 0.863269 |
| | | | | Average | 0.775763 |
| 121.9 [c] | 1 | 148.73 | 203.1 | 195.82 | 0.896101 |
| | 2 | 140.39 | 199.41 | 195.24 | 0.911284 |
| | 3 | 138.33 | 198.51 | 198.69 | 0.928096 |
| | 4 | 132.01 | 195.96 | 199 | 0.942936 |
| | 5 | 130.44 | 194.99 | 199.12 | 0.947129 |
| | 6 | 133.34 | 196.93 | 201.73 | 0.949377 |
| | | | | Average | 0.929154 |

Figure 9:
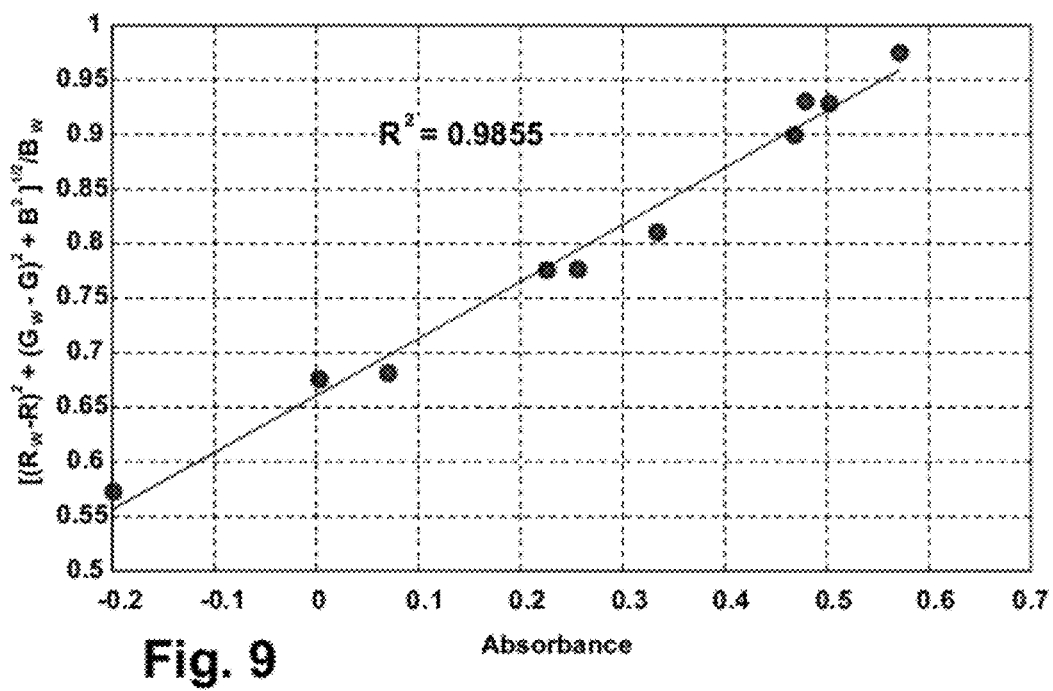
FIG. 9 is a graph that illustrates the correlation of $[(Rw-R)^2+(Gw-G)^2+B^2]^{1/2}/B_w$ to absorbance measured with a optical reflectance probe at 650 nm.

[a] Solutions prepared from $Na_2CO_3$
[b] Solutions prepared from a mixture of $Na_2CO_3$, $NaHCO_3$, and $Na_2HPO_4$. The percentage alkalinity contributions of $Na_2CO_3$, $NaHCO_3$, and $Na_2HPO_4$ are 10%, 80%, and 10%, respectively.
[c] Solutions prepared from $NaHCO_3$ In FIG. 8, the average $R_{alk}$ value of the six films is plotted as a function of solution alkalinity Note that the calibration curve for alkalinity analysis is not necessarily a straight line. The curvature in the calibration curve is not due to the current color analysis method. This is supported by the linear correlation of $R_{alk}$ to absorbance measured with the spectrophotometer at 650 nm as shown in FIG. 9.

EXAMPLE 5

Figure 10:
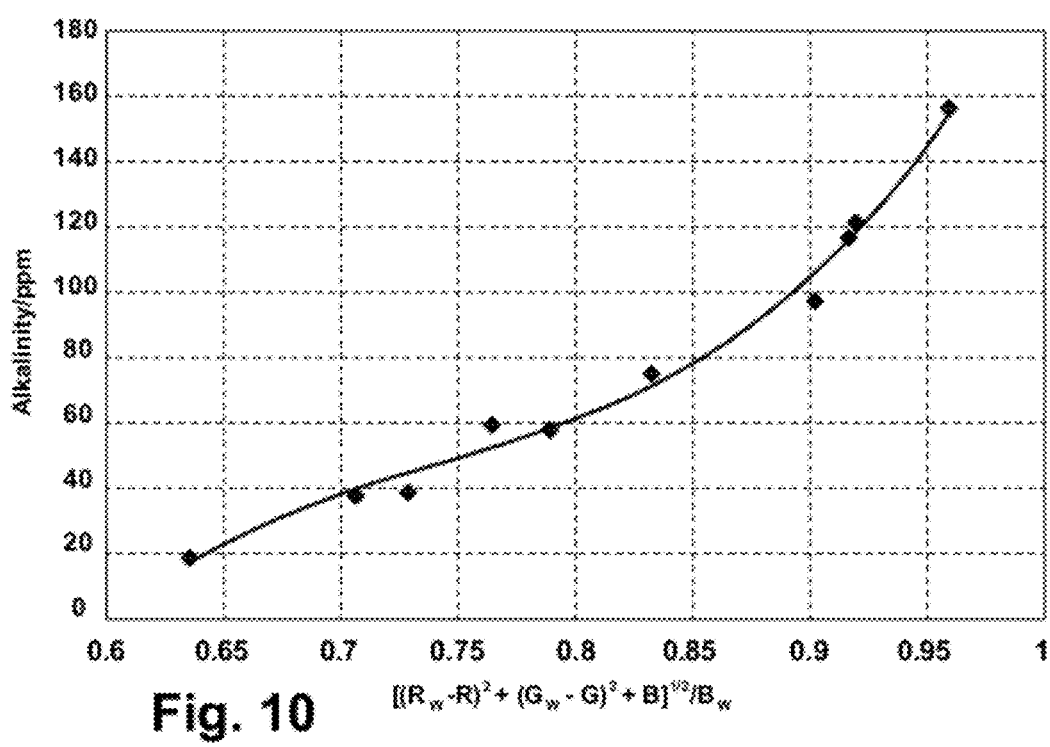
FIG. 10 is a graph that illustrates $[(R_w-R)^2+(G_w-G)^2+B^2]^{1/2}/B_w$ calculated from a digital image captured by a color digital camera plotted a function of solution alkalinity.

Determination of Alkalinity Using a Digital Camera—Normalization Against Internal Reference Areas The image of total 60 films was captured with Sony DSC S75 digital camera. The camera was set in the automatic mode in which white balance, focusing, and aperture were automatically adjusted. The glass slides were placed near a 40-Watt desk lamp Average RGB values for the selected color areas are listed below in Table 4. Unlike the image captured by a digital scanner, illumination cross the subject is not uniform. In order to correct this, RGB values of a white paper background near each film were taken. Instead using a single set of RGB values for the white background in Equation 3, each color film has a set of $R_w G_w B_w$ values, as listed in Table 4 below. The calibration curve is shown FIG. 10.

TABLE 4

Color analysis of the digital camera image for Example 5

| Film # | R | G | B | Rw | Gw | Bw | R(alk) |
|---|---|---|---|---|---|---|---|
| 18.8 ppm | | | | | | | |
| 1 | 140.86 | 143.1 | 84.25 | 162.69 | 157.08 | 135.4 | 0.651018 |
| 2 | 140.67 | 142.3 | 82.65 | 165.08 | 159.68 | 137 | 0.641711 |
| 3 | 146.04 | 147.05 | 84.465 | 168.13 | 161.59 | 140.64 | 0.629325 |
| 4 | 147.2 | 147.73 | 85.82 | 170.18 | 164.35 | 142.98 | 0.632149 |
| 5 | 153.32 | 153.27 | 89.03 | 172.23 | 166.67 | 144.92 | 0.634814 |
| 6 | 154.87 | 156.16 | 88.95 | 174.44 | 169.12 | 147.71 | 0.622807 |
| | | | | | | Average | 0.635304 |
| 37.7 ppm | | | | | | | |
| 1 | 131.98 | 146.95 | 98.97 | 169.39 | 164.92 | 144.31 | 0.743674 |
| 2 | 134.93 | 144.73 | 95.6 | 168.45 | 162.99 | 142.68 | 0.721466 |
| 3 | 136.82 | 144 | 89.99 | 167.09 | 161.07 | 141.07 | 0.683823 |
| 4 | 137.45 | 141.81 | 88.41 | 164.71 | 158.89 | 137.82 | 0.682634 |
| 5 | 133 | 140.36 | 96.32 | 162.02 | 156.08 | 134.82 | 0.755211 |
| 6 | 137.23 | 138.96 | 81.32 | 158.58 | 153.87 | 131.44 | 0.649633 |
| | | | | | | Average | 0.706073 |
| 75.5 ppm | | | | | | | |
| 1 | 116.72 | 144.57 | 110.98 | 174.52 | 168.4 | 146.2 | 0.871262 |
| 2 | 117.94 | 148.16 | 114.66 | 177.59 | 170.89 | 149 | 0.880748 |
| 3 | 120.48 | 150.52 | 115.13 | 178.24 | 172.04 | 150.85 | 0.865707 |
| 4 | 123.11 | 153.27 | 113.07 | 180.76 | 174.86 | 153.65 | 0.837891 |
| 5 | 132.76 | 156.82 | 111.64 | 182.99 | 177.51 | 156.33 | 0.794189 |
| 6 | 140 | 159.85 | 107.86 | 184.27 | 179.33 | 158.15 | 0.747441 |
| | | | | | | Average | 0.832873 |

TABLE 4-continued

Color analysis of the digital camera image for Example 5

| Film # | R | G | B | Rw | Gw | Bw | R(alk) |
|---|---|---|---|---|---|---|---|
| 39.0 ppm | | | | | | | |
| 1 | 157.33 | 167.69 | 116.34 | 187.75 | 181.8 | 161.13 | 0.75142 |
| 2 | 152.09 | 166.7 | 113.08 | 186.53 | 180.76 | 159.11 | 0.748171 |
| 3 | 150.41 | 163.15 | 109.64 | 185.09 | 179.19 | 157.94 | 0.735136 |
| 4 | 152.52 | 161.57 | 107.71 | 182.21 | 176.47 | 154.05 | 0.731686 |
| 5 | 153.53 | 160.2 | 107.31 | 180.93 | 174.54 | 152.83 | 0.730729 |
| 6 | 154.42 | 158.39 | 96.93 | 178.45 | 172.23 | 150.17 | 0.671364 |
| | | | | | | Average | 0.728084 |
| 58.5 ppm | | | | | | | |
| 1 | 130.39 | 144.37 | 108.43 | 169.76 | 163.45 | 141.56 | 0.825964 |
| 2 | 130.02 | 147.89 | 110.69 | 173.18 | 166.58 | 145.38 | 0.827266 |
| 3 | 125.14 | 148.35 | 105.91 | 174.06 | 168.29 | 146.3 | 0.808982 |
| 4 | 133.16 | 152.51 | 105.58 | 176.9 | 170.27 | 148.63 | 0.778131 |
| 5 | 137.64 | 155.4 | 111.67 | 178.51 | 172.87 | 152.09 | 0.790259 |
| 6 | 148.67 | 158.85 | 102.81 | 179.85 | 175.19 | 154.16 | 0.704914 |
| | | | | | | Average | 0.789253 |
| 97.5 ppm | | | | | | | |
| 1 | 106.9 | 154.16 | 124.43 | 181.09 | 175.61 | 154.76 | 0.946293 |
| 2 | 107.42 | 152.28 | 120.38 | 179.55 | 174.12 | 152.9 | 0.928874 |
| 3 | 109.2 | 150.24 | 117.63 | 177.87 | 171.84 | 150.24 | 0.917926 |
| 4 | 107.62 | 146.64 | 113.12 | 174.96 | 169.24 | 147.67 | 0.904533 |
| 5 | 124.06 | 148.49 | 113.67 | 174 | 167.34 | 147.23 | 0.852947 |
| 6 | 118.91 | 143.63 | 110.02 | 170.08 | 163.88 | 142.39 | 0.863934 |
| | | | | | | Average | 0.902418 |
| 117.0 ppm | | | | | | | |
| 1 | 102.02 | 139.66 | 111.68 | 170.9 | 164.47 | 143.33 | 0.931683 |
| 2 | 99.01 | 141.84 | 112.46 | 174.03 | 167.55 | 146.01 | 0.942463 |
| 3 | 103.35 | 144.47 | 114 | 175.36 | 168.9 | 147.89 | 0.926593 |
| 4 | 106.92 | 147.08 | 117.41 | 177.91 | 172.32 | 149.94 | 0.930408 |
| 5 | 115.69 | 152.03 | 117.52 | 179.77 | 174.24 | 152.46 | 0.889973 |
| 6 | 121.83 | 155.64 | 120.84 | 181.74 | 176.32 | 155.59 | 0.876998 |
| | | | | | | Average | 0.916353 |
| 156.0 ppm | | | | | | | |
| 1 | 114.04 | 147.2 | 117.91 | 174.8 | 168.63 | 146.92 | 0.914541 |
| 2 | 104.21 | 148.52 | 121.67 | 178.71 | 173.28 | 150.76 | 0.960464 |
| 3 | 100.84 | 150.88 | 121.22 | 180.18 | 174.49 | 152.95 | 0.959709 |
| 4 | 100.89 | 153.52 | 126 | 182.97 | 177.44 | 155.97 | 0.976259 |
| 5 | 101.37 | 155.15 | 127.03 | 184.47 | 179.49 | 158.37 | 0.970738 |
| 6 | 104.23 | 157.53 | 130.45 | 186.1 | 180.74 | 160.09 | 0.972901 |
| | | | | | | Average | 0.959102 |
| 60.0 ppm | | | | | | | |
| 1 | 122.73 | 135.27 | 98.11 | 160.28 | 154.92 | 131.5 | 0.812717 |
| 2 | 116.3 | 136.7 | 94.48 | 163.61 | 157.33 | 135.23 | 0.796112 |
| 3 | 120.64 | 139.51 | 99.26 | 165.64 | 158.85 | 138.02 | 0.801963 |
| 4 | 127.22 | 142.71 | 95.65 | 168.63 | 161.2 | 141.11 | 0.75017 |
| 5 | 133.11 | 146.56 | 97.41 | 169.92 | 163.69 | 141.93 | 0.743554 |
| 6 | 144.59 | 151.32 | 93.69 | 170.84 | 165.67 | 144.44 | 0.680908 |
| | | | | | | Average | 0.764237 |
| 121.9 ppm | | | | | | | |
| 1 | 115.97 | 158.69 | 127.09 | 176.25 | 170.76 | 149.63 | 0.943514 |
| 2 | 113.09 | 157.26 | 124.81 | 172.85 | 169.22 | 148.45 | 0.935635 |
| 3 | 115.71 | 155.67 | 121.02 | 174.25 | 168.47 | 147.28 | 0.916913 |
| 4 | 117.18 | 154.2 | 120.59 | 172.42 | 166.52 | 144.39 | 0.922578 |
| 5 | 117.79 | 151.55 | 117.27 | 170.7 | 163.44 | 141.64 | 0.912184 |
| 6 | 122.59 | 149.93 | 113.83 | 167.05 | 159.76 | 138.39 | 0.885897 |
| | | | | | | Average | 0.919454 |

Figure 11:
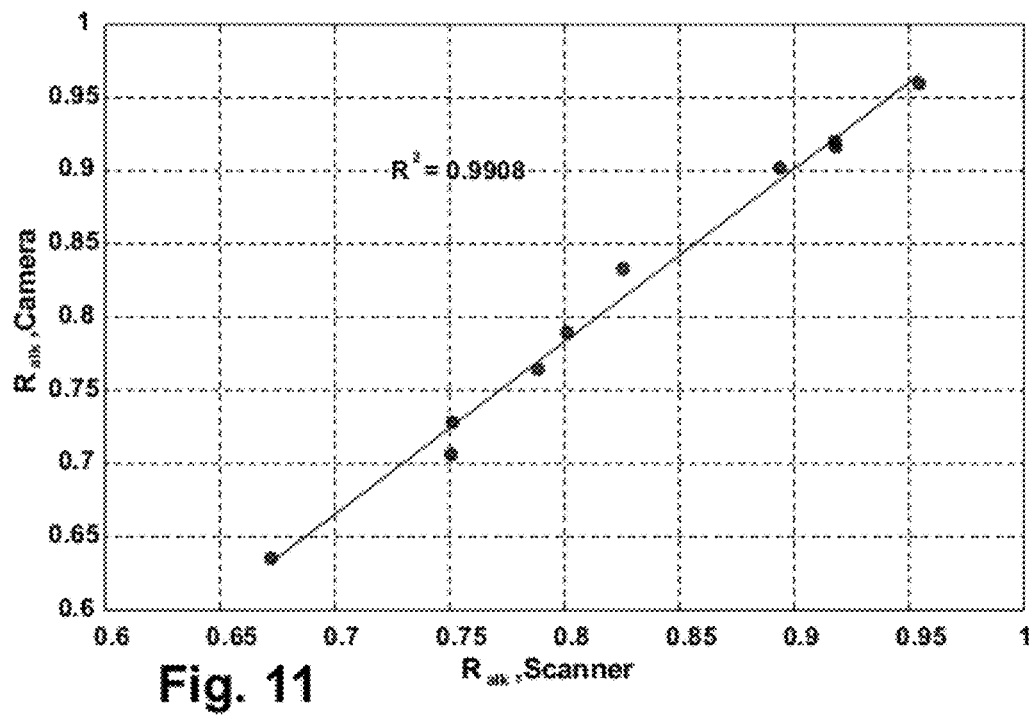
FIG. 11 is a graph that illustrates performance of the camera vs. scanner.

The image in this example was captured about 36 hours after the image in Example 2 was taken. In order to compare the digital camera results with those obtained with scanners, another image was prepared using Canon N650U scanner at the same time when the camera image was taken. Correlation of the relative blue intensity from the Canon scanner to that from Sony digital camera is shown in FIG. 11. The result shown in FIG. 11 indicates that normalization against an internal color reference can effectively eliminate errors caused by non-uniform illumination when a camera is used to capture the sensor image.

EXAMPLE 6 pH Determination by Means of Multivariate Calibration

A pH sensitive film was deposited on a polycarbonate sheet. The film contains pH indicator dye bromothymol Blue and other additives. The pH standard solutions used in this example were prepared from sodium carbonate and sulfuric acid solutions. A glass electrode, calibrated against two pH buffers (7.00 and 10.00 from Fisher Scientific, traceable to NIST standards), was used to measure pH values for the standard solutions. No correction was made for the ionic strength effects on hydrogen ion activity coefficient and liquid junction potentials. Alkalinity was measured by titration against a 0.2 N sulfuric acid solution.

A 40 μl aliquot of the pH standard solution was spotted on the film. The sample was removed after 2 minutes, and the spotted area was dried by a modest blow of airflow. Digital images of the film before exposure and after exposure were captured with using Canon LiDE 80 scanner in 48-bit color mode with 300 dpi spatial resolution. The image file was saved in the uncompressed TIFF format. Photoshop CS was used to retrieve RGB values from the file. The RGB values listed below in Table 5 were averaged over a 1000-pixel square centered at the spotted area. The following quantity $R_{pH}$ is chosen as a sensor response to quantify sample pH:

$$R_{pH} = (R/G - B/G)_{exposed} - (R/G - B/G)_{unexposed} \quad \text{Equation (4)}$$

Figure 12:
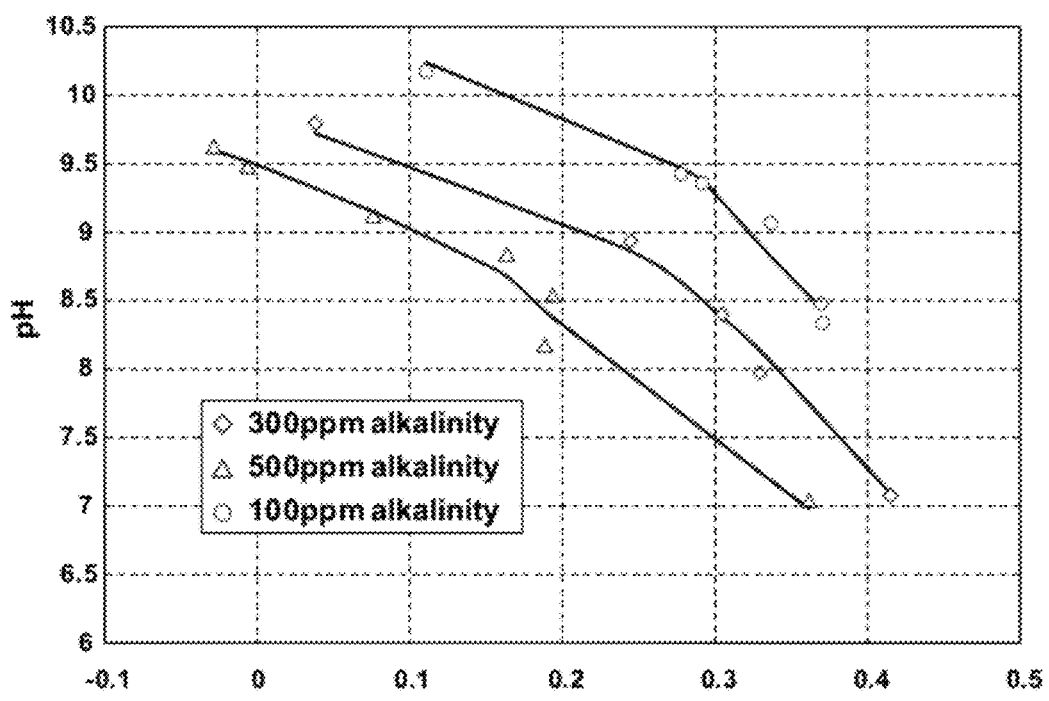
FIG. 12 is a graph that illustrates the multivariate calibration of pH determination.

The sensor responses are plotted as a function of sample pH and alkalinity in FIG. 12. It is clear from FIG. 12 that the sensor response is a function of both sample pH and alkalinity as described in the above section. It was found that experimental pH values could fit into the following two-variable calibration equation within 0.09 pH unit (average absolute deviation).

$$pH = a_0 + a_1 \text{alk} + (a_2 + a_3 \text{alk}) R_{pH} + (a_4 + a_5 \text{alk})(R_{pH})^2 \quad \text{Equation (5)}$$

Values of fitting parameters a0 to a5 are listed below in Table 6. The pH values calculated from the above equation are compared with experimental values in Table 6.

TABLE 6

Parameters for the pH calibration equation and pH values calculated from the calibration equation

| Response | Alkalinity/ppm | pH_calculated | pH_Measured | Difference |
|---|---|---|---|---|
| 0.3705 | 97.4 | 8.45 | 8.34 | 0.11 |
| 0.3695 | 100.6 | 8.45 | 8.48 | 0.03 |
| 0.3365 | 112.4 | 8.83 | 9.07 | 0.24 |
| 0.2917 | 92.4 | 9.39 | 9.36 | 0.03 |
| 0.2778 | 103.2 | 9.47 | 9.43 | 0.04 |
| 0.1106 | 100.0 | 10.25 | 10.18 | 0.07 |
| 0.0376 | 303.2 | 9.73 | 9.80 | 0.07 |
| 0.2447 | 311.0 | 8.86 | 8.94 | 0.08 |
| 0.3045 | 303.6 | 8.38 | 8.40 | 0.02 |
| 0.3293 | 301.8 | 8.14 | 7.97 | 0.17 |
| 0.4150 | 308.6 | 7.10 | 7.08 | 0.02 |
| 0.3617 | 510.8 | 6.98 | 7.04 | 0.06 |
| 0.1884 | 516.8 | 8.42 | 8.18 | 0.24 |
| 0.1933 | 506.0 | 8.43 | 8.54 | 0.11 |
| 0.1634 | 490.0 | 8.70 | 8.84 | 0.14 |
| 0.0755 | 504.0 | 9.16 | 9.12 | 0.04 |
| −0.0062 | 500.0 | 9.52 | 9.48 | 0.04 |
| −0.0286 | 492.0 | 9.60 | 9.63 | 0.03 |

Parameters for equation 3 in example 4

| A0 | A1 | A2 | A3 | A4 | A5 |
|---|---|---|---|---|---|
| 10.067 | −0.00113 | 7.8279 | −0.02317 | −20.2109 | 0.04331 |

TABLE 5

Color analysis of digital images for Example 6

| | | Unexposed | | | Exposed | | | Response |
|---|---|---|---|---|---|---|---|---|
| PH | Alkalinity/ppm | R | G | B | R | G | B | $R_{pH}$ |
| 8.34 | 97.4 | 93.45 | 175.28 | 158.23 | 87.61 | 157.64 | 139.94 | 0.3705 |
| 8.48 | 100.6 | 94.67 | 177.02 | 159.89 | 109.57 | 161.73 | 129.58 | 0.3695 |
| 9.07 | 112.4 | 94.06 | 176.91 | 159.30 | 117.92 | 164.81 | 128.52 | 0.3365 |
| 9.36 | 92.4 | 92.97 | 175.08 | 158.03 | 120.91 | 166.85 | 127.96 | 0.2917 |
| 9.43 | 103.2 | 93.95 | 176.48 | 159.21 | 136.19 | 173.50 | 128.34 | 0.2778 |
| 10.18 | 100.0 | 93.67 | 176.33 | 158.83 | 125.32 | 165.97 | 125.32 | 0.1106 |
| 9.80 | 303.2 | 93.84 | 176.33 | 158.82 | 124.92 | 169.49 | 130.35 | 0.0376 |
| 8.94 | 311.0 | 93.23 | 175.63 | 158.26 | 116.49 | 165.61 | 129.50 | 0.2447 |
| 8.40 | 303.6 | 94.13 | 177.03 | 159.34 | 115.52 | 165.44 | 130.51 | 0.3045 |
| 7.97 | 301.8 | 102.17 | 178.73 | 158.17 | 101.40 | 161.05 | 134.05 | 0.3293 |
| 7.08 | 308.6 | 93.67 | 176.33 | 158.83 | 125.32 | 165.97 | 125.32 | 0.4150 |
| 7.04 | 510.8 | 94.91 | 176.01 | 156.53 | 118.66 | 156.56 | 116.85 | 0.3617 |
| 8.18 | 516.8 | 95.42 | 176.31 | 156.27 | 100.98 | 155.56 | 125.36 | 0.1884 |
| 8.54 | 506.0 | 98.57 | 177.33 | 156.99 | 102.86 | 153.85 | 123.80 | 0.1933 |
| 8.84 | 490.0 | 94.21 | 175.45 | 155.48 | 97.51 | 154.32 | 126.18 | 0.1634 |
| 9.12 | 504.0 | 99.25 | 177.38 | 157.83 | 95.49 | 158.61 | 135.89 | 0.0755 |
| 9.48 | 500.0 | 101.78 | 177.08 | 155.51 | 86.71 | 150.73 | 133.38 | −0.0062 |
| 9.63 | 492.0 | 97.58 | 176.17 | 157.58 | 82.32 | 151.37 | 138.21 | −0.0286 |

EXAMPLE 7

Noise Reduction

Several solid sensor films have been produced with defects that were caused by undissolved reagents of the sensor film formulation prepared from a polymer solution. Some defects were introduced in the film preparation steps, such as inclusion of dust particles in the film. Foreign materials could be deposited on the film during the exposure to the sample matrix. A digital image provides very high spatial resolution on color intensity distribution over each sensor region. This spatial information can be exploited for noise reduction. A variety of data analysis tools can be used to reduce errors resulted in by the film defects. This example demonstrates a simple statistical approach to reject readings from the defect areas.

Figure 13:
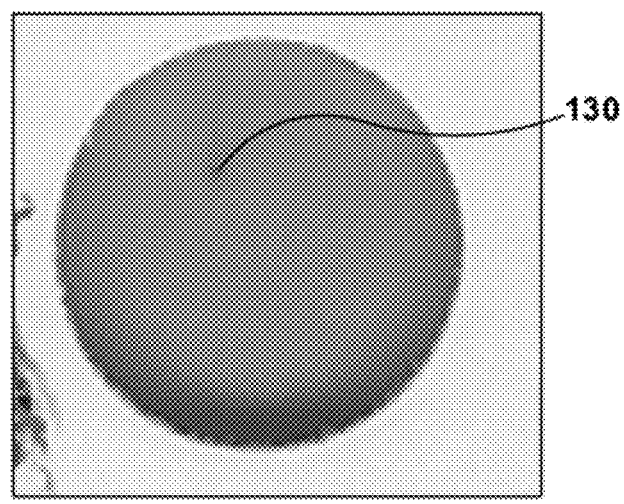
FIG. 13 shows a pH sensor film with defects.
Figure 14:
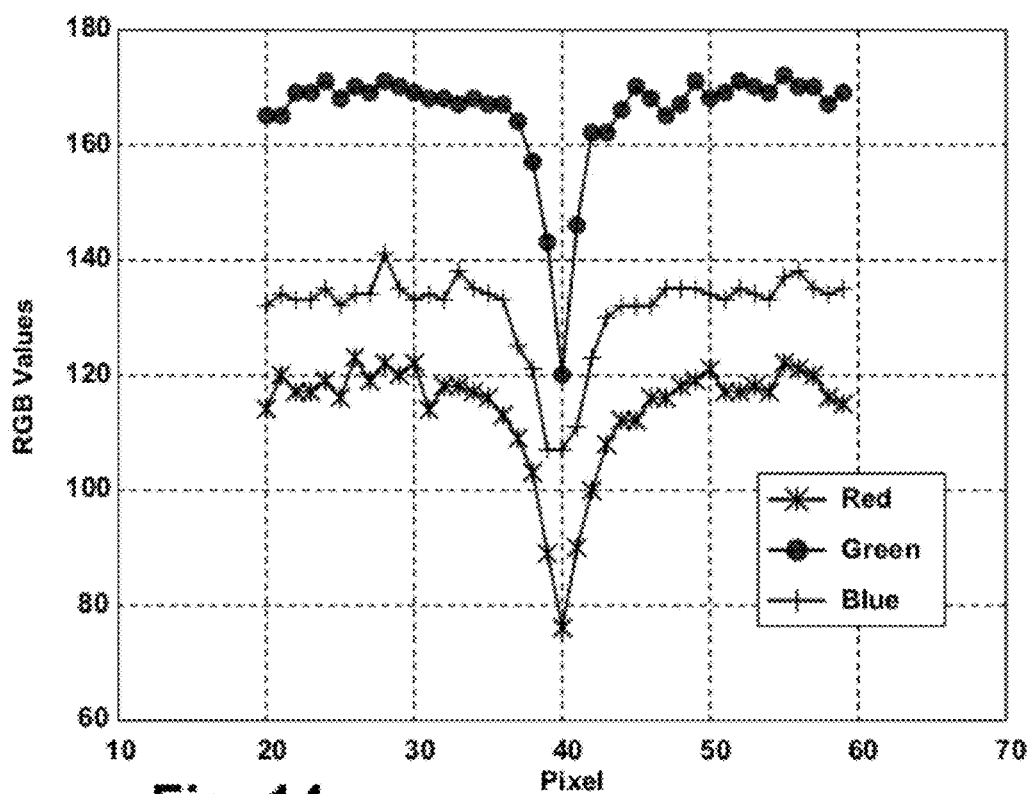
FIG. 14 is a graph that illustrates the effects of film defect on RGB values.

An enlarged color image of a pH sensor spot taken from Example 6 is shown in FIG. 13. A dust particle, indicated by the reference number 130, is visible in this image. RGB values for a 40-pixel horizontal line containing this dust particle are shown in FIG. 14. In Example 6, RGB values averaged over the whole sensor region are used to calculate the sensor response. For simplicity, we use one-dimensional data in this example to demonstrate the noise reduction method. We first calculate averages and standard deviations of this data set respectively for R, G, and B. Then, we reject those points with deviation from the set average greater than a pre-set multiple of the standard deviation for the set. Finally, averages and standard deviation are calculated from pixels excluding the dust areas.

Figure 15:
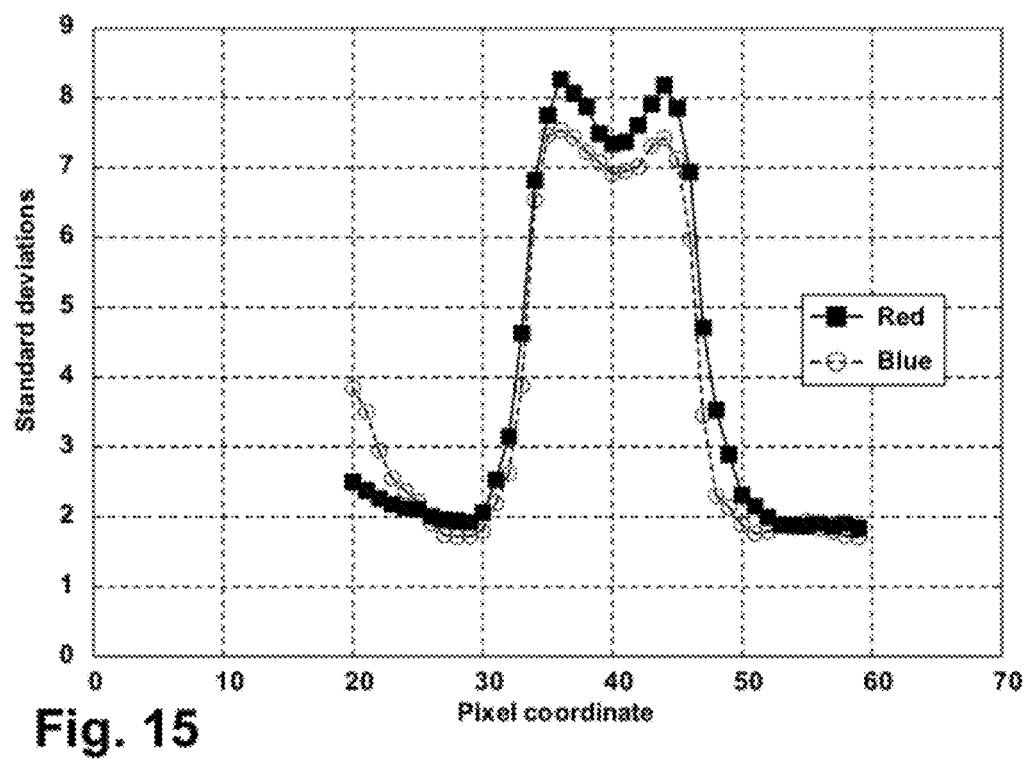
FIG. 15 is a graph that illustrates the rejection of a group of pixel by standard deviation criteria.

A similar calculation can be used to reject a group of pixels. We first calculate the standard deviations for the whole sensor regions. Then, we calculate standard deviations within a smaller area (a 6-pixel circle chosen for this example) centered at each pixel along each horizontal pixel line. FIG. 15 shows results from these calculations. It is clear that an area centered at the 40th pixel should be rejected.

Figure 16:
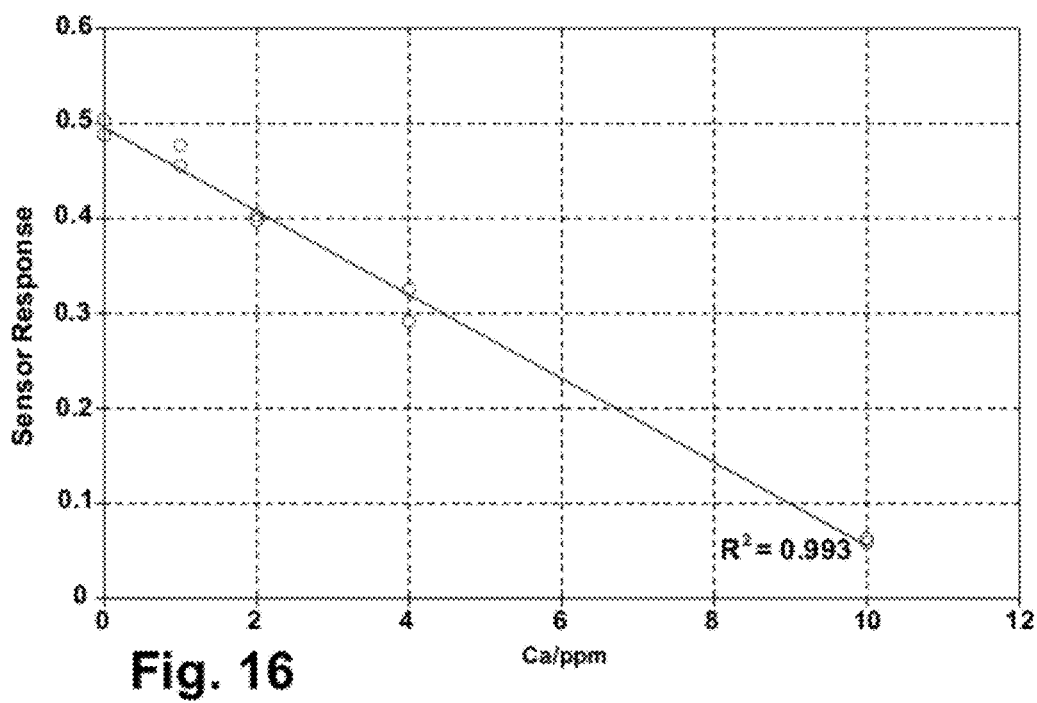
FIG. 16 is a graph that illustrates the calibration curve for Ca sensor film.

FIG. 16 shows a calibration curve for a calcium sensor film. The film was prepared from a polymer solution, which contains a calcium responsive dye. The film was prepared on a polycarbonate sheet with a film applicator. When the film is dry, some dye aggregate to form small dark areas randomly distributed across the entire film, barely seen by naked eyes. A digital image of the exposed film was scanned with Canon LiPE 80 scanner in 16-bit color mode with 300 pdi spatial resolution. The same equation as used for pH calibration was used to calculate the sensor response. The data filtering methods described above (2× standard deviation) was used to rejected data points originated from the dye aggregates. Generally, 90 to 145 pixels are rejected among a 2700 pixel area. The R-squared value of the calibration is 0.9930, which is significantly improved compared to 0.9886 obtained with un-filtered RGB values retrieved using Photoshop CS.

EXAMPLE 8

Kinetic Response

Figure 18:
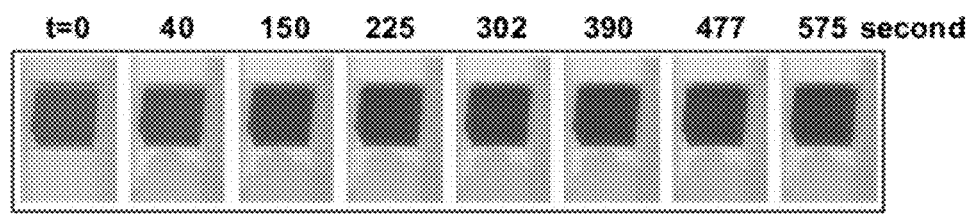
FIG. 18 comprises digital images showing color change of the molybdate sensor film during the course of its exposure to a water sample at 25.3° C.

A polymer solution containing molybdate sensing reagents was prepared. The polymer solution was deposited on a polycarbonate sheet using a film applicator. The polycarbonate substrate was cut into 20×80 mm strips. The bulk of sensor film on each strip was cut and removed, which left only a 6×6 mm sensor spot on the strip. A 200 µm deep, 6.5 mm wide channel was built using a glass slide and double-sided tapes to cover the 6×6 spot to form a fluidic assembly. This assembly, a Canon LiPE 80 scanner, and a 10-ppm molybdate standard solution were placed in a temperature-controlled room. After an equilibration for about one hour, sample solution was introduced to the sensor film through the channel by capillary action. Images of the sensor film were acquired at time intervals shown in Table 7 below. Images obtained at 25.3° C. are shown in FIG. 18.

In this example, we want to demonstrate the importance of data analysis for sensor responses, which is an important part of the systematic method for simultaneously determination of multiple analytes disclosed in this invention.

It was found that the initial sensor response of an unexposed film is a function of temperature. For convenience, we normalize the sensor response after exposure by calculating the ratio below to quantify molybdate concentration:

$$R_{Mo} = (R/G - B/G)_{exposed} / (R/G - B/G)_{unexposed} \qquad \text{Equation (6)}$$

TABLE 7

Kinetic data at three temperatures

| Time/s | R | G | B | $R_{Mo}$ |
|---|---|---|---|---|
| T = 4.5° C. | | | | |
| 0 | 198.71 | 81.40 | 65.34 | 1.0000 |
| 21 | 185.96 | 87.22 | 84.94 | 1.4146 |
| 68 | 179.06 | 88.60 | 88.85 | 1.6092 |
| 112 | 173.74 | 87.29 | 87.22 | 1.6530 |
| 170 | 171.18 | 86.73 | 86.79 | 1.6839 |
| 221 | 169.87 | 87.04 | 87.22 | 1.7255 |
| 294 | 168.82 | 87.03 | 87.33 | 1.7498 |
| 486 | 168.50 | 87.36 | 88.05 | 1.7792 |
| 612 | 168.62 | 87.68 | 88.51 | 1.7933 |
| T = 25.3° C. | | | | |
| 0 | 196.73 | 74.73 | 56.43 | 1.0000 |
| 40 | 189.06 | 71.78 | 64.43 | 1.0813 |
| 150 | 154.68 | 68.59 | 66.73 | 1.4642 |
| 225 | 148.57 | 67.56 | 65.76 | 1.5317 |
| 302 | 146.36 | 67.57 | 65.83 | 1.5753 |
| 390 | 144.61 | 67.31 | 65.70 | 1.6014 |
| 477 | 143.61 | 67.09 | 65.51 | 1.6128 |
| 575 | 142.10 | 67.67 | 66.06 | 1.6708 |
| T = 34.5° C. | | | | |
| 0 | 200.69 | 78.13 | 56.06 | 1.0000 |
| 34 | 199.14 | 76.14 | 62.32 | 1.4146 |
| 83 | 189.60 | 76.14 | 70.23 | 1.6092 |
| 133 | 184.29 | 76.8 | 74.20 | 1.6530 |
| 221 | 175.36 | 74.87 | 73.91 | 1.6839 |
| 326 | 165.41 | 71.69 | 70.92 | 1.7255 |
| 409 | 160.84 | 70.20 | 69.45 | 1.7498 |
| 514 | 158.14 | 69.54 | 68.75 | 1.7792 |
| 588 | 157.16 | 69.49 | 68.78 | 1.7933 |

Figure 17:
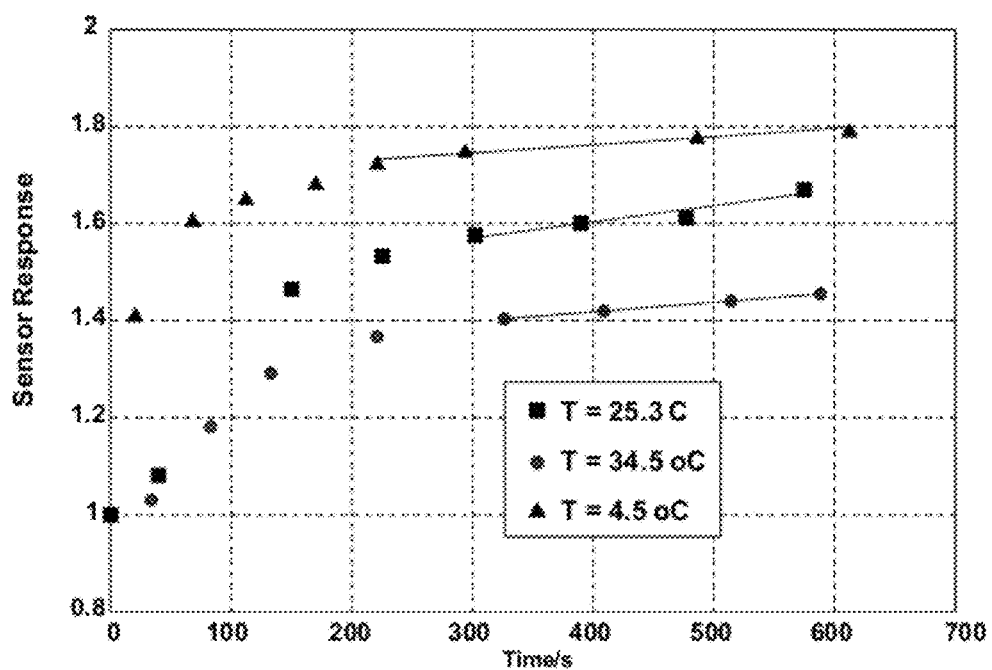
FIG. 17 is a graph that illustrates kinetic response of molybdate sensor film at different temperatures.
Figure 19:
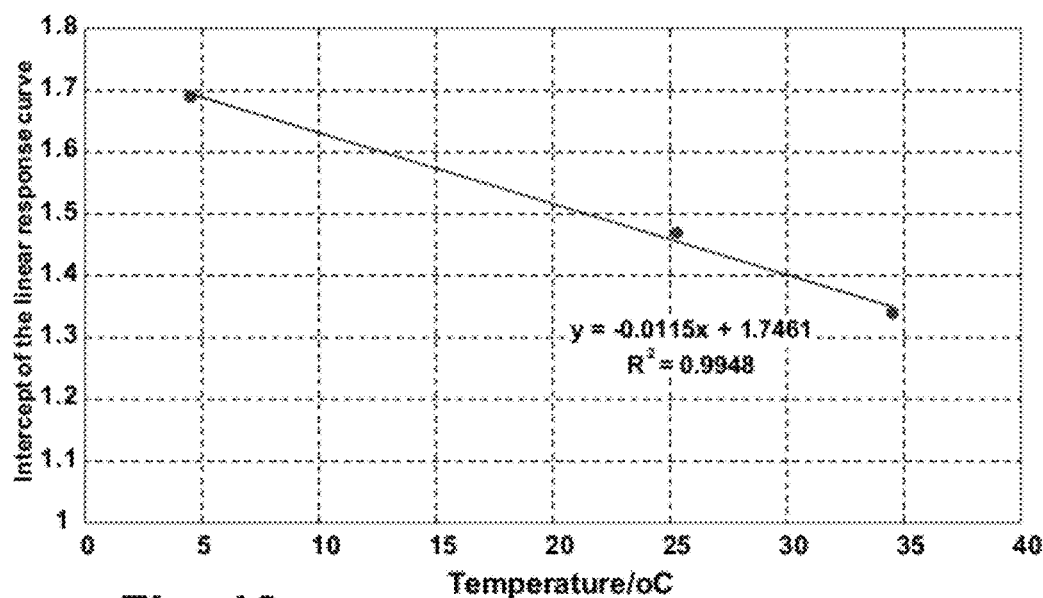
FIG. 19 is a graph that illustrates temperature effect on molybdate sensor response.

This quantity is plotted as a function of time in FIG. 17. Unlike many chemical sensor reactions, the sensor response as defined above does not reach a plateau. It rather continues to increase linearly with time. Linear fits of the last four points for each temperature are shown in FIG. 19.

Taking a single reading from this unsteady film response may result in a large error. For this type of sensor response, we intend to use a quantity derived from the kinetic measurement to quantity the analyte concentration. It is found that the intercepts of the linear curves shown in FIG. 17 are a linear function of temperature. Thus, a multivariate-calibration equation, in which temperature and the sensor responses at several exposure times are independent variable, is suitable for this type of sensor.

Those who are familiar with the art would recognize that many statistical and mathematic models could be used to interpret the kinetic data presented in this example. The methods include Kalman filtering, least square fitting, and other time series prediction tools as detailed in analytical literature.

EXAMPLE 9

Sample-volume Controlled Sensor Array

Eight magnesium sensitive sensor films were screen printed on a 127.8×85.0 mm polycarbonate sheet. A sample delivery device, similar to that described in Example 2, was put on the top the polycarbonate sheet to form enclosed channels and reservoirs. The sensor films are 4 mm long, 4 mm wide, and about 0.01 mm thick. The reservoirs are 5.25 mm long, 5.25 mm wide, and 1.6 mm deep. The volume of the reservoirs is 44.1 µl. When sample is introduced to the central entry port, the capillary force drives the sample to fill the reservoirs. This delivery device provides a volume controlled sample distribution means for the sensor array.

A custom-made 4×4 LED/photodiode array detector was used to monitor the sensor film response. The LEDs have emission maximum at 467, 530, and 634 nm. The LEDs and photodiodes were fixed on two separated print circuit boards. The print circuit boards were held parallel inside an enclosure, where the sensor array assembly can be inserted and aligned with the LED/photodiode array.

Figure 23:
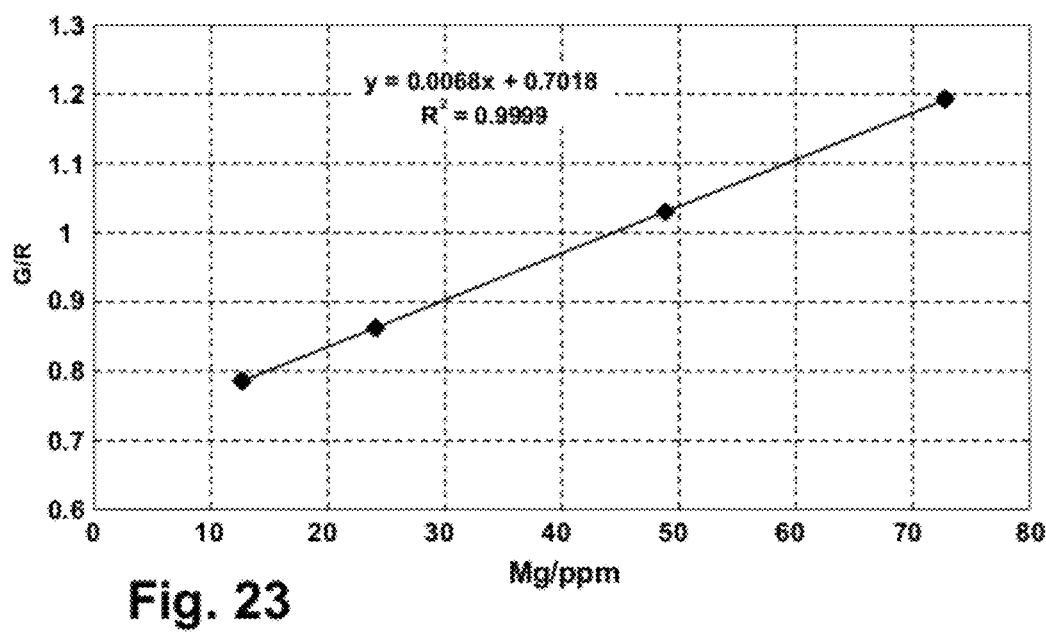
FIG. 23 is a calibration curve for the magnesium sensitive film obtained with a sample-volume controlled sampling device detailed in Example 9.

A 3.0 ml water sample containing 12 to 100 ppm magnesium was first introduced to the sample entry port. The sensor absorbance at 530 nm (G) 634 nm (R) was measured 3 minutes after sample introduction. It was found that the ratio G/R is linear with respect to magnesium concentration in the sample. The calibration curve is shown in FIG. 23.

We also disclose sampling methods and systems for delivering controlled volumes of fluid samples to sensor arrays. One application of the present invention is to provide means for delivering controlled volumes of liquid samples to sensor arrays on optical disks. Methods for producing sensor arrays on optical disks are described in several of our prior patent applications, for example U.S. Patent Application 2005/0112358, U.S. Patent Application 2005/0111000, U.S. Patent Application 2005/0111001, and U.S. Patent Application 2005/0111328, the disclosures of which are all hereby incorporated by reference herein.

In accordance with exemplary embodiments of the present invention, we provide sampling systems and methods wherein a fluid sampling system is comprised of a removable sampling structure located in proximity to an array of chemically sensitive sensor regions located on a substrate. The removable sampling structure permits each sensor region to individually interact with sample fluid introduced into the sampling system.

Figure 24:
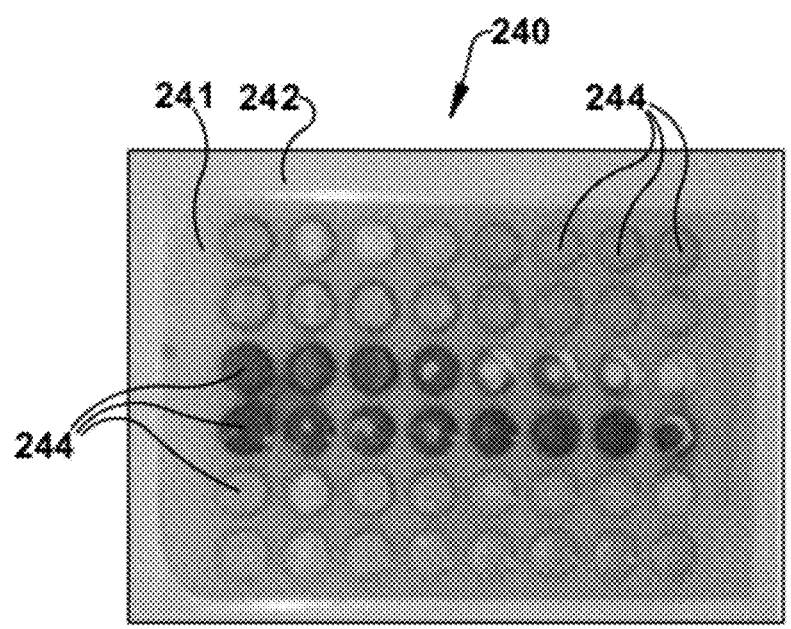
FIG. 24 is a photograph depicting a soft material sampling layer mounted to a substrate with sensor elements in accordance with an exemplary embodiment of the present invention upon exposure of the elements to controlled sample volumes of liquid in each reservoir.

FIG. 24 shows an exemplary sampling system 240 incorporating a soft material sampling layer 241 detachably mounted to a substrate 242 having a plurality of sensor regions 244. The sensor regions 244 may be integrally formed with the substrate 242 or may be disposed on a bottom surface of the layer 241. The layer 241 may be mounted to the substrate 242, for example, by a reversible adhesive. The exemplary sampling system 240 and the sensor regions 244 were exposed to controlled volumes of sample fluid in each reservoir.

Figure 25:
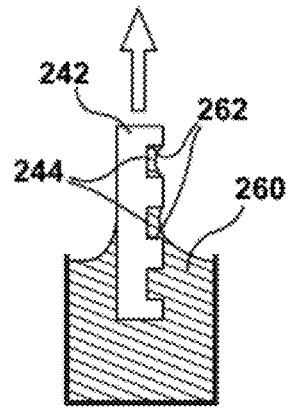
FIG. 25 illustrates a literature example of a liquid filling an array of reservoirs as the substrate is removed from the sample volume.

FIG. 25 illustrates the literature concept of vertical dipping a substrate 242 and attached reservoirs 262. As shown in FIG. 25, the substrate/reservoir structure is dipped in a sample fluid 260 in order to fill each reservoir 262 with a sample volume of fluid. Next, when the substrate 242 is removed from the liquid 260 (as indicated by the upward arrow), a controlled portion of the sample volume is maintained in each reservoir by the surface tension of the walls of the reservoir, even though the reservoirs 262 are oriented substantially vertical to the surface of the fluid 260 when the substrate 242 is removed. In this exemplary embodiment, the reservoirs 262 may be formed with an attached reservoir-formed sampling layer (not shown) adhered to the substrate 242 as described above.

Figure 27:
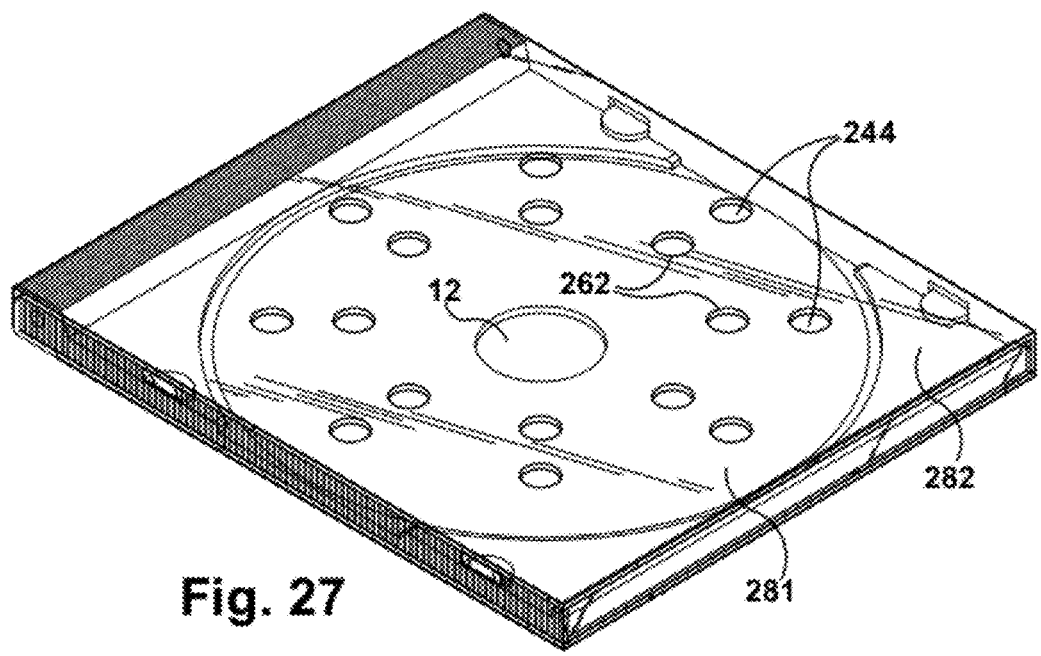
FIG. 27 is a perspective view of an exemplary fluidic sampler in the form of a DVD and disk case with an entry port in the middle of the disk for fluid introduction.

As best shown in FIG. 27, the present invention also contemplates providing means for delivering controlled volumes of liquid samples to sensor arrays located on optical disks 281. To demonstrate fluid delivery to a DVD, CD, Super-audio CD, double-layer, blu-ray disk and/or to other types of substrates, we fabricated the sampler device shown in FIG. 27. Here, there is illustrated a concept wherein the substrate is a DVD disk 281 comprising a plurality of sensor regions 244. The device illustrates the use of individual open or partially closed reservoirs 262 on top of each of the sensor regions 244. The exemplary sampling system therefore takes the form of a DVD disk 281 enclosed in a disk case 282 with sensor regions 244 and a fluid entry port 12 located in the middle of the disk 281.

As shown in FIG. 27, the sensor optical disk such as DVD, CD, Super-audio CD, double-layer, blu-ray disk and the like is contained in a jewel (i.e. disk) case 282. The optical disk 281 is assembled with a detachable sample layer configured in accordance with FIG. 1. Additionally, the disk case 282 contains a blotting layer that serves to remove residual water from the disk before measurement. The blotting layer is made of any porous material that is capable of absorbing water through contact with the substrate.

Figure 26:
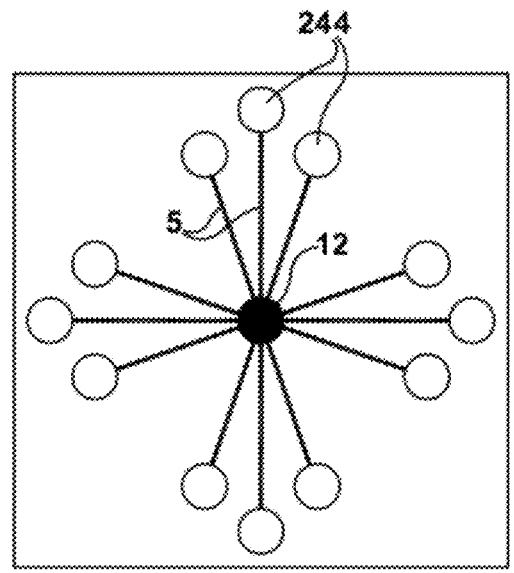
FIG. 26 illustrates a channel-reservoir configuration for delivering samples to multiple sensor regions from an entry point on a single substrate.

FIG. 26 illustrates an exemplary tree-type structure for introduction of fluid samples from a fluid entry port 12 to multiple sensor regions 244 directed by a plurality of fluidic channels 5. It is understood by those skilled in the art that many different methods may be used for moving the fluids through the sampling system including electro-osmotic flow, capillary force, electro-wetting (wherein electrocapillary pressure is created by a conductive liquid that shares a capillary with a confined insulating liquid), thermo-capillary pumping (involving temperature gradients in capillaries), magnetic fields, surface directed flow (surface tension in capillaries, chemically modified surfaces), electrochemical control (redox-active surfactants for valving), mechanical means (syringes, pressure initiated forces), centripetal (including spinning liquids), and surface energy gradients, and/or combinations thereof.

It is understood that the present invention is adapted for operation in reflection, transmission, emission, and/or scatter modes of analysis. It is also understood that the present invention can be applied to different types of sensor arrays and can be operated in the step-wise or continuous modes. In the step-wise mode, sensor array operation and readout can be performed before and after, or only after the sensor elements have been exposed to the sample liquid. In the continuous mode, sensor array operation and readout can be performed during the liquid exposure. To accommodate the different modes of operation, the sampling layer structure may be removed from the substrate before measurement occurs, or the structure may be kept intact during the measurement process.

In further aspects of the present invention, the total analysis system includes an optical array platform comprising diverse chemically or physically responsive sensor materials in a form of water-swellable films or/and water-dissolvable films or/and water-leachable films The system produces an optical response proportional to the desired chemical or physical parameter, provides secondary effect reduction from noise, defect, and interference effects, compensates for multivariate interactions, accounts for test array history, and provides a reference system to calibrate the sensor array response to the optical detection platform. This complex test array can be combined with time-based data acquisition to provide temporal test analysis that can further enhance overall array response. The array elements described herein show how each element enhances the array performance, and how the combination of these elements can be used to produce optimized environmental and biological measurements. Further, this enhanced optical array platform is advantageously suited for non-laboratory environments.

Another aspect of the invention is each sensor element or film is exposed to a controlled sample volume. Two different fluid delivery systems are disclosed herein for the transport and dosing of sample liquid to the sensor elements that is required to effect a chemical reaction between the sample liquid and the sensor element. The two delivery systems described below are a capillary-flow-based fluidic delivery device and a dip-cell based fluidic delivery device. Both the fluid delivery devices of the present invention are capable of being combined with the test array card comprising of the sensor elements described herein.

Another aspect of the invention is each sensor element is exposed to a controlled sample volume where the sensor element is in a form of a water-swellable film or/and water-dissolvable film or/and water-leachable film. Because of the controlled sample volume, the chemical reagents in the film responsible for the generation of the optical signal upon interaction of water with the sensor element stay in the sample volume, providing an accurate signal measurement.

Test Array Card

Figure 28:
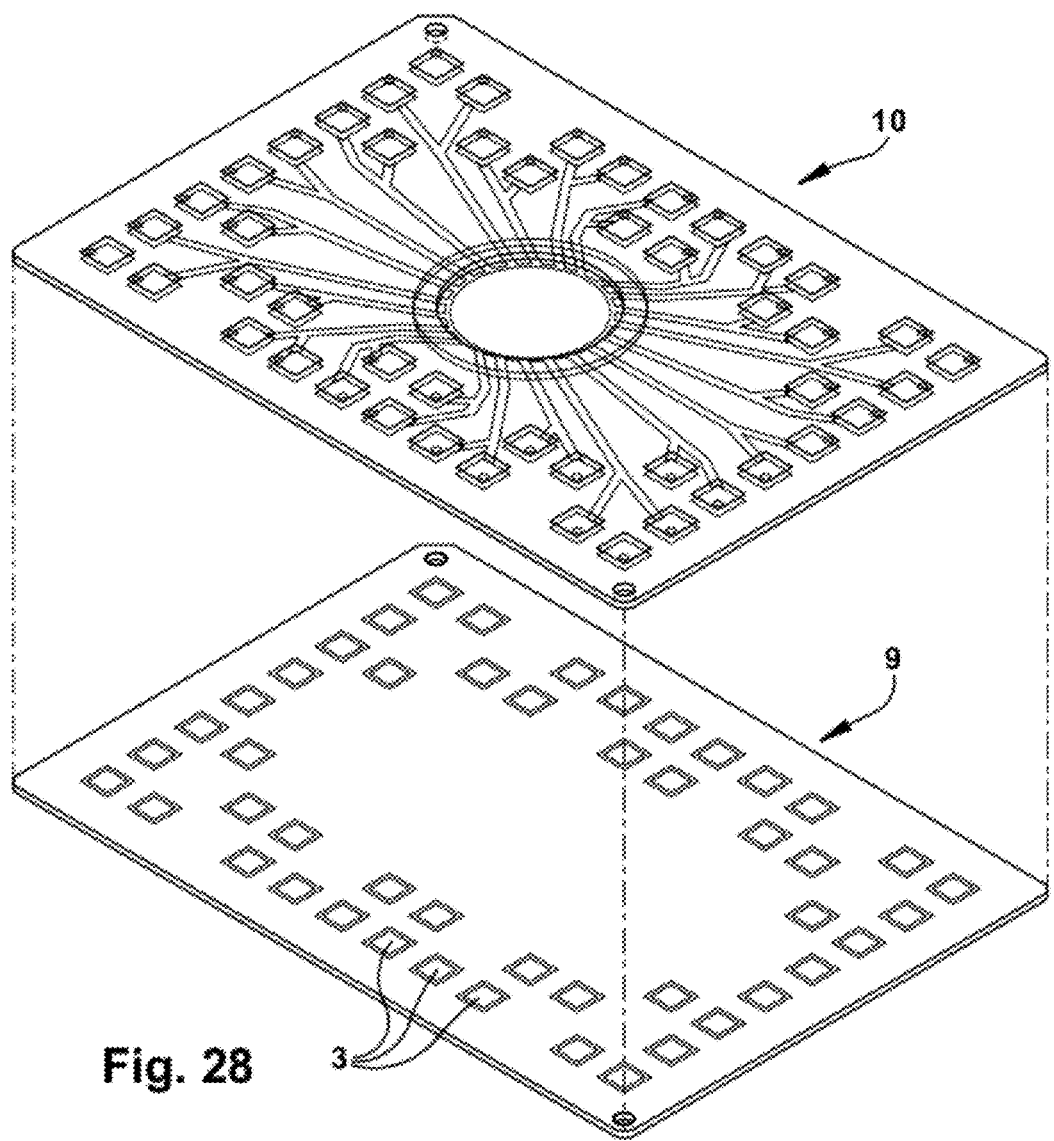
FIG. 28 is a perspective view of a fluidic delivery device in accordance with an exemplary embodiment of the present invention as prepared for assembly.

FIG. 28 illustrates a single-use or disposable test array card 9, also referred to as a disk or substrate, comprising diverse chemically or physically responsive sensor films 3 in accordance with an exemplary embodiment of the present invention. The sensor films 3 can be grouped into chemical or physically similar sets of one or more films depending on the desired fidelity of a sensor response through the use of outlier elimination or statistically processing of the individual film responses.

Fluidic Delivery Device

Figure 29:
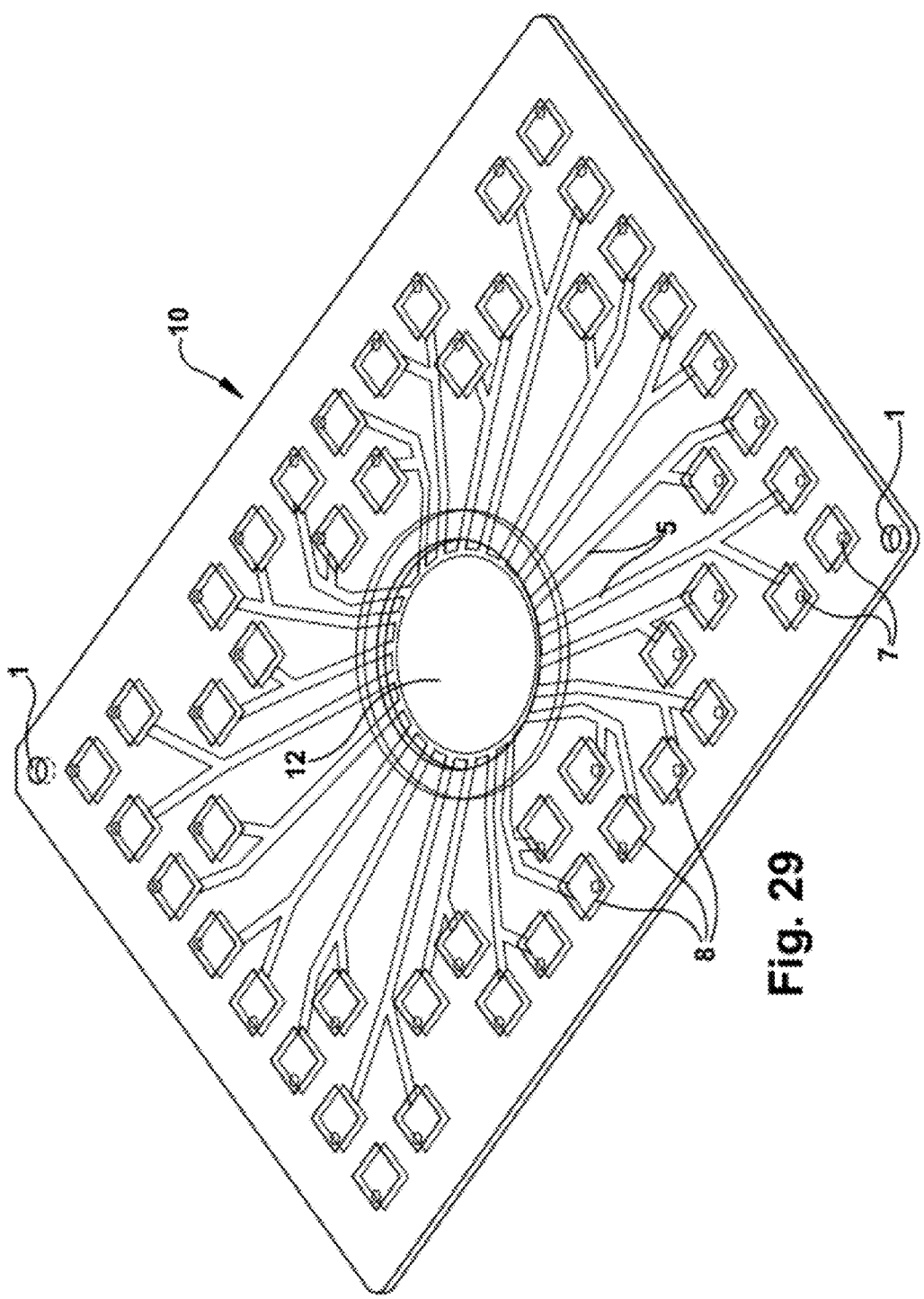
FIG. 29 is a perspective view of the fluid delivery device of FIG. 28 as assembled.

FIG. 29 illustrates a fluidic delivery device 10 that can be aligned and assembled to the test array card 9 using the locating holes 1. The delivery device 10 transports a controlled amount of a liquid sample injected at the entry port 12, in metered quantities, to an array of reservoirs 8 through channels 5 radiating out of the entry port 12 to the reservoirs 8 in order to effect a chemical reaction between the sample fluid and the sensor element 3 connected to the cell. In addition the fluidic delivery device provides four sidewalls and the roof of the reservoirs with the test array card 9 providing the bottom floor. The roof of the reservoirs comprises a film that has circular vent holes 7 that vent air out of the reservoirs as they are filled with sample liquid. The vent hole material, diameter and depth are optimized to regulate the effective venting of air and containment of sample fluid within the controlled dimensions of walls of the reservoirs 8. The hydrophobic walls of the cylindrical vent hole 7 are critical to keeping the sample fluid contained in the reservoir even in instances when the fluid-delivery device is subject to a tilt relative to the horizontal plane resulting from conducting the measurement on typically bench-top surfaces that may deviate slightly from an absolute level of zero degrees.

Referring again to FIG. 1, an exemplary fluidic delivery device configured in accordance with an exemplary embodiment of the present invention generally comprises, but is not limited to, four components, namely: an O-ring 11 with an adhesive or other common polymer welding methods applied to bind to components of the delivery device and effectively creating a holding and containing wall for the injected sample fluid; a cover seal film 2 fabricated from a hydrophobic plastic material (e.g., polypropylene, oriented polypropylene, polyethylene terephthalate, and the like) that has a modified hydrophilic bottom surface by means of coating, chemical treatment, surface modification and the like to create the roof of the reservoirs 8 and material removed in the roof to create air venting holes 7 on the top of channels 5 and wells or reservoirs 8; a fluidic channel plate 4 with several through-thickness openings to create the side walls of the wells or reservoirs 8 that are connected to the entry port 12 by shallow grooves or channels 5 cut into the plate on the top surface plane of fluidic channel plate 4; and a bind layer 6 adapted to attach the bottom surface of fluidic channel plate 4 to the sensor array plate (not shown)—the bind layer construction being either a screen-printable adhesive, a double-coated adhesive tape, or a soft silicone sheet with the property of high wettability deposited on the bottom of the fluidic channel plate 4 or on the free top surface of the test array card 9.

Another aspect of this invention is that the components in the fluidic delivery device, for instance, the bind film 6 and the O-ring 11 that in one embodiment are comprised of double-coated adhesive tape or screen-printed adhesive to bind to other components of the fluidic delivery device should exhibit an insignificant chemical interference with the response of the sensor elements. Adhesives in such applications typically belong to family of acrylate-based adhesives. Careful screening of the adhesive system is preferred to minimize chemical interferences.

In another embodiment of the fluidic delivery device, the O-ring is a partially absorbent material that is hydrophobic at the center and is hydrophilic towards the outer diameter. This allows any excess water injected into the entry port that spills over the top due to a splash or tilt of the fluidic delivery device to the horizontal plane to be absorbed by the porous material. This minimizes any excess injected sample fluid from running off to the top of the cover seal film 2 and resulting in increased and uncontrolled introduction of sample fluid to the plurality of reservoirs from surface vent holes 7 or possible cross-contamination through carryover of reacted sample fluid from one or more reservoirs to others from the surface route and down the vent holes 7.

In one embodiment of the test array platform, the fluidic delivery device is combined with the test array card during the measurement. Within this embodiment, the body of fluid sample is allowed to reside in the reservoir of sample fluid interacting with the sensor element during the measurement, i.e., the measurement is done "wet" as the reaction occurs or proceeds towards an equilibrium.

In the above embodiments of the test array platform wherein the test array card is combined with the fluidic delivery device during the measurement, the cover seal film may comprise transparent materials so that a minimal intensity of the source light in the wavelength range of interest is absorbed by this layer assuming that the light is incident on the sensor elements and needs to transmit through the thickness of this component.

Figure 30A:
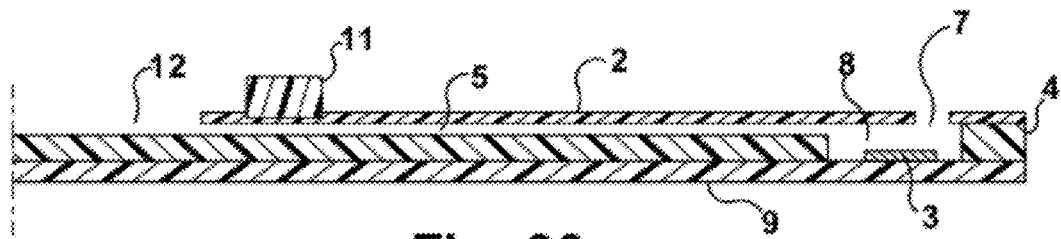
FIGS. 30a-30c are cross-section views of exemplary embodiments of the present invention.
Figure 30B:
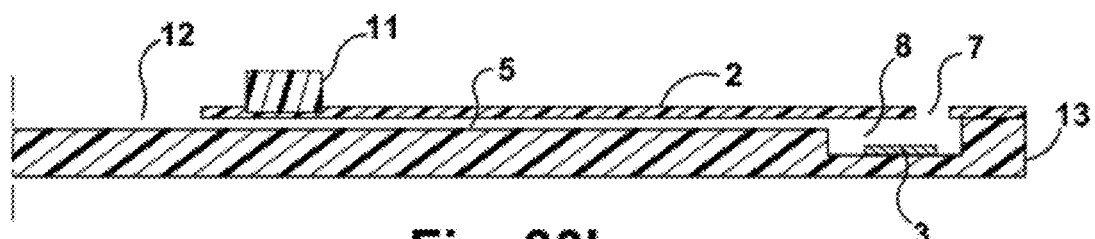
Figure 30C:
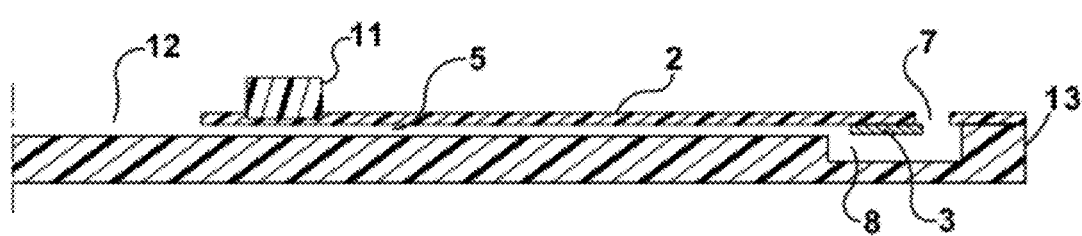
Figure 31B:
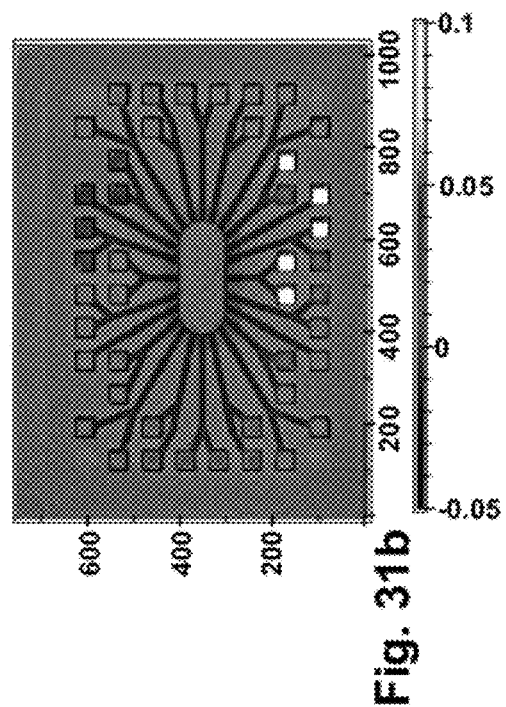
FIGS. 31a-31d illustrate dynamic absorbance imaging of operation kinetics of the assembled sampler at different stages of filling of the sampler with a water sample.
Figure 31D:
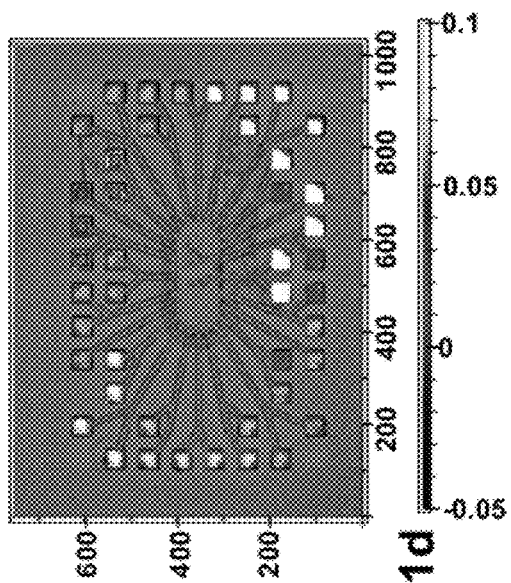
Figure 31A:
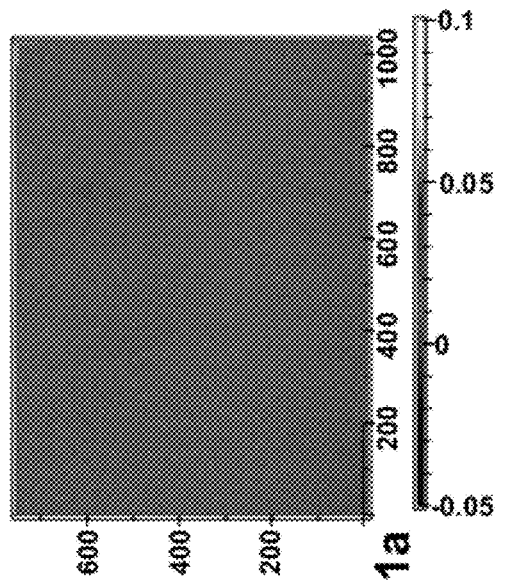
Figure 31C:
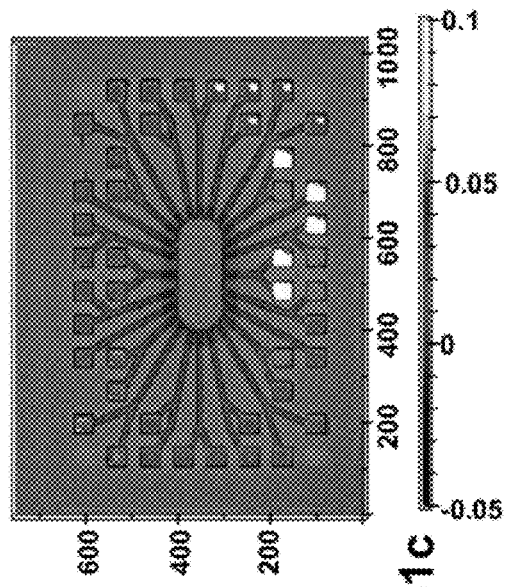

With reference now to FIGS. 30*a-c*, the fluidic sampling device may comprise a fluidic channel plate 4 attached to the test array card 9, wherein the cover layer 2 forms the roof portion of the reservoirs 8 and vent holes 7 and forming the fluidic channels 5 communicating with the entry port 12 sealed by O-ring 11 (FIG. 30*a*). Alternatively, as best shown in FIGS. 30*b-c*, the combined fluidic channel test array 13 may comprise sensor elements 3 disposed within the reservoirs 8 (FIG. 30*b*) or the sensor elements 3 may be disposed on the bottom surface of the cover layer 2 (FIG. 30*c*).

The sensor elements 3 may be integrated into the fluidic-delivery system and the combined fluidic channel test array 13 is modified to include a plurality of wells 8 instead of through-thickness openings of a separate fluidic channel plate 4 that forms the four walls of the reservoir. Such embodiments also eliminate the need for a bind layer 6 since there is no longer a separate test array card 9. The advantage of such embodiments is that it reduces the total number of components to be assembled for the test array platform to generally three components, namely: an O-ring 11, a cover seal film 2, and a modified fluidic-channel plate 13 that includes wells for containing the sample fluid. Within such embodiments, the sensor elements may be placed on top of the sample fluid (i.e., bottom surface of cover layer 2) rather than on the bottom (i.e., within the reservoir 8), as is the case for other embodiments described herein.

In yet another embodiment of the test array platform, a molded plate designed to contain an O-ring feature at the topside replaces the cover film 2 The O-ring/cover plate combination retains all the venting features and hydrophilic bottom surface of the film. This embodiment allows reduction of components to be assembled to two for increasing manufacturing efficiency.

In another embodiment of the total analysis system, the fluidic delivery device 10 is detachable from the test array card 9. Within this embodiment, the test array card 9 is dried to the extent that no sample fluid droplets remain on the surface of sensor elements 3. The test therefore consists of an additional absorbing step wherein after the reservoirs are filled and adequate time is allowed for the sensor elements to react, the fluidic delivery device is separated from the test array card also resulting in sample fluid from the reservoirs transporting away along the peel interface. The remaining water droplets on the surface of the sensor elements are preferably absorbed away with an absorbent sheet before the test array card is introduced into the detecting device for measurement of the sensor element responses. A characteristic of this embodiment is that the absorbent material will have a controlled range of surface characteristics, i.e., wicking characteristics including absorption rate and liquid capacity to effectively remove the sample fluid from the surface of the sensor elements without creating undesirable deformation at the surface of the sensor elements as a result of rapid fluid removal. The dip-cell-based fluidic delivery system disclosed herein may also be referred to as a detachable fluidic-delivery system embodiment.

Hydrophilic-Coated Hydrophobic Cover Film/Plate

Most common plastics such as poly (ethylene) terephthalate, polycarbonate, polystyrene, poly (methyl) methacrylate, polyethylene, polypropylene, nylon, ABS, and the like have contact angles with water ranging from about 60° to about 110°. In this exemplary embodiment, the present invention comprises a combination of hydrophilic surfaces in contact with the fluidic channels and sample reservoirs connecting the two in a continuous single plane forming the roof of the channel-reservoir structure. The two sidewalls of the channels, the channel floor and four sidewalls of the reservoir are generally surfaces of a typical plastic with contact angles about 65-90°. The combination of contact angle from these walls does not provide the required capillary force to drive fluid flow from the fluid introduction area through the channels and into the reservoirs. The importance of the hydrophilic surface of the cover film/plate is that it augments the channel and reservoir construction and helps draw the fluid sample into the channels from the holding area, propel the flow through the channel towards the reservoirs, and subsequently helps transition from the channel into the reservoir along the roof. The fluid is rapidly drawn to accumulate along the roof and drawn down into the reservoir with the help of gravity force and capillary forces along the edges of the reservoir walls. The hydrophilicity of this surface of the cover film/plate is qualified by requiring the contact angle to be preferably lower than about 30 degrees, and more preferable lower than about 20 degrees. Typically, engineering plastic materials do not have contact angles of 30 degrees or lower. Therefore, to overcome this characteristic, the bottom surface of the hydrophilic cover film/plate is preferably modified to a hydrophilic surface by way of surface physical modification, surface chemical treatment, surface coating, or surface polarity-enhancing methods.

The hydrophilic coated cover film 2 shown in FIG. 1 is preferably obtained from Adhesives Research Inc. as ARFlow® 90128. This film advantageously provides for easy assembly to the fluidic channel plate 4 by incorporating an adhesive ingredient in the blend of the hydrophilic coating applied to one-side of the backing film. The backing film can be a variety of films formed by film extrusion, blown-film, or film casting. However it is advantageous to have a film with a high contact angle such as polypropylene which comprises a contact angle ranging from about 90-110 degrees. Generally speaking, the greater the contact angle, the better the ability of the fluidic delivery device to prevent the water in the reservoir from seeping out of the vent holes due to manufacturing variations in the vent dimensions, or spatial variations in surface properties of the polymer film, or incidence of tilt to the test-array system during a measurement keeping the fluid from spilling out or over-dosing to the reservoir.

Referring again to the embodiment shown in FIG. 1, the cover film coating is a blend of both hydrophilic and adhesive active ingredients of the type available from Adhesives Research as ARFlow® 90128 film. In this embodiment, no additional binding material is required to assemble the cover film/plate with the fluidic channel plate. Although it is convenient to use a hydrophilic/adhesive coated cover film that combines hydrophilic and adhesive properties in the components for producing a fluidic device, it may be desirable in some embodiments to produce a hydrophilic surface by using an additional step particularly in the cover plate embodiment described above that replaces the cover film with a O-ring featured plate. In this regard, it is understood that polyvinyl pyrrolidone has been used extensively in the literature to hydrophilize surfaces of polymer surfaces, membranes, and filters.

Like the preceding examples, the following examples are included to demonstrate the broad applicability of the present invention. It should be appreciated by those of skill in the art that the techniques disclosed in the examples which follow represent techniques discovered by the inventors, and thus can be considered to constitute exemplary modes for its practice. However, those of skill in the art should, in light of the present disclosure, appreciate that many changes can be made in the specific embodiments which are disclosed and still obtain a like or similar result without departing from the scope of the invention.

EXAMPLE 10

A polyethylene film coated on one side with a silicone release film was soaked in a 1% solution of polyvinyl pyrrolidone (PVP) overnight at 40° C. The heat promotes the bonding of PVP to the polymer film and makes the surface hydrophilic. This coated film was used in place of the cover film 2 in FIG. 1. The fluidic channel plate 4 was sprayed with a 3M-spray adhesive and the PVP coated film was laminated to the plate and using other elements of FIG. 1, a test array system incorporating the fluidic cover was produced. The filling profiles of 44 cells in the test array system using PVP coated polymer film for hydrophilic flow are shown in FIG. 33 using Acid blue 80 dye measured using identical number of LED-PD pairs at 630 nm wavelength.

Figure 33:
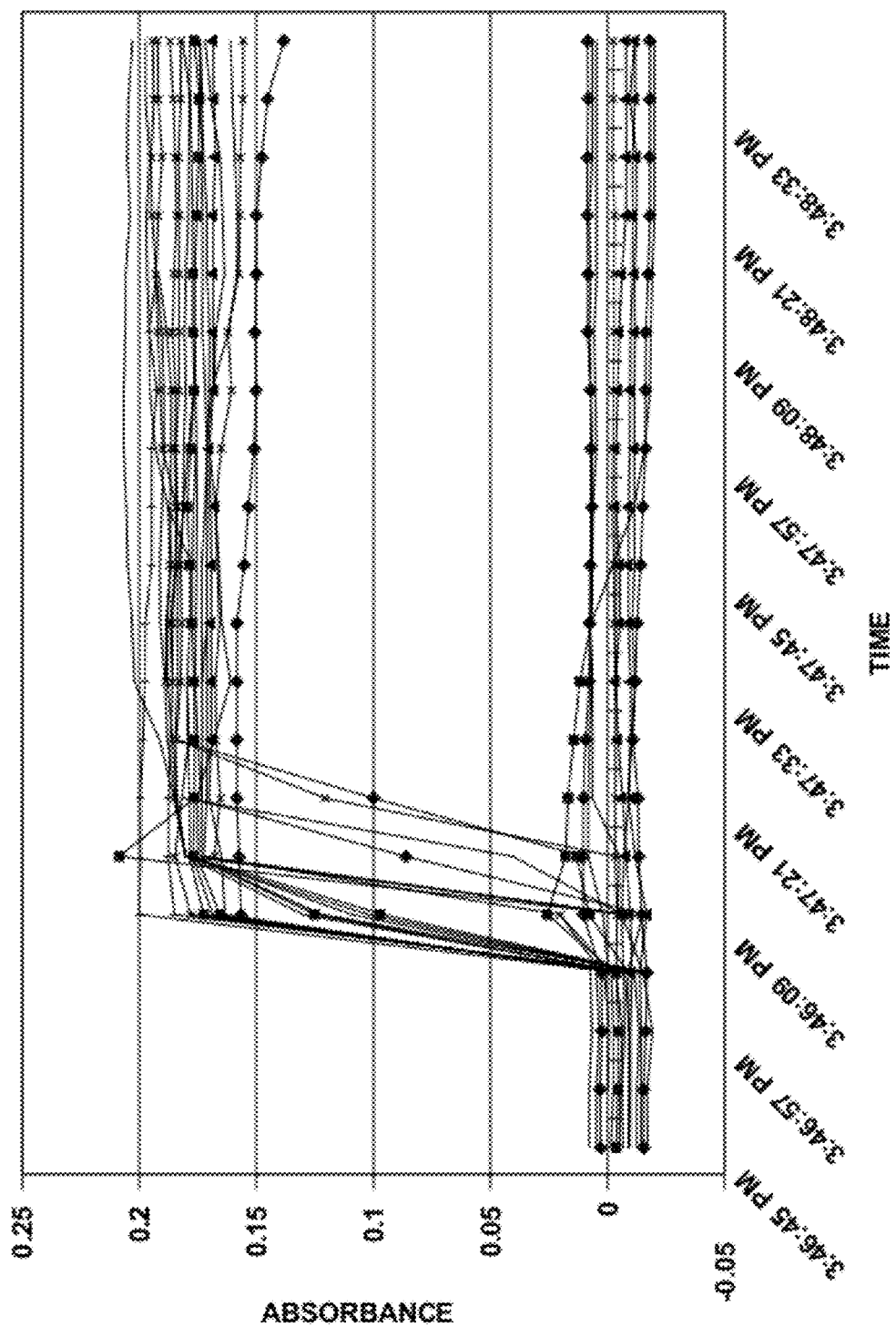
FIG. 33 is a graph illustrating absorbance measurements collected at six second time intervals from a time before the sample was injected to the point when the cells were completely filled.

The profiles shown in FIG. 33 consist of absorbance measurements collected at 6 seconds time-intervals from a time before the sample was injected (no sample in the cells) to the point when the cells were completely filled (showing an absorbance of ~0.2). The profiles that do show an increase in absorbance either were not connected by channels or were in an area of the PVP-coated film that did not effectively coat with the PVP solution.

Since the cover film/plate is directly in the optical path of the sensor system for several of the embodiments described herein, the plastic is chosen to be suitable for transparent film/plate. However, in one of the alternate embodiments of the fluidic device that is detachable, a polymer that forms translucent or opaque film/plate can also be considered.

EXAMPLE 11

As shown in FIGS. 31a-d, dynamic absorbance imaging of operation kinetics of the assembled sampler are shown at different stages of filling of the assembled sampler with a water sample. Here, dynamic absorbance imaging was performed to evaluate the operation kinetics of the assembled sampler. In these measurements, the image in FIG. 31a of a dry assembled sampler was taken as a reference, and the images shown in FIGS. 31b-d were taken at different stages of filling of the sampler, respectively. In this evaluation, performance of individual sensor elements was evaluated simultaneously.

EXAMPLE 12

As shown in FIGS. 32a-c, dynamic absorbance imaging was performed to evaluate the operation kinetics of assembled sampler with sensor elements that provide controlled leaching of reagents into the controlled sample volume. Here, dynamic absorbance imaging of operation kinetics of assembled sampler are shown at different stages of filling of the assembled sampler with a water sample. The left-top and left-bottom quadrants of each FIGS. 32a, 32b, 32c did not contain sensor elements, and therefore show a very uniform water-filling kinetics. The right-top and right-bottom quadrants of each FIGS. 32a, 32b, 32c also contain replicate sensor elements and show a very uniform water-filling kinetics and reagent-release kinetics. Because of the controlled sample volume, the chemical reagents in the film responsible for the generation of the optical signal upon interaction of water with the sensor element stay in the sample volume, providing an accurate signal measurement. In these measurements an image of a dry assembled sampler was taken as a reference as shown in FIG. 32a. In this evaluation, performance of individual sensor elements was evaluated simultaneously.

Dip Sample Delivery

FIGS. 34a, 34b illustrate yet another embodiment of the present invention. As shown in FIGS. 34a, 34b, a mask made of a suitable hydrophobic material (e.g. silicone, neoprene, and the like) with holes that act as sample reservoirs is positioned on top of a substrate 350 containing sensor films. The reservoirs 352 in the mask 354 can be produced by methods including molding, punching, cutting, drilling and the like. The diameter of the reservoirs (which are numbered 1-12) combined with the thickness of the mask defines the sample volume capacity of the reservoirs 352. The mask 354 may be attached to the substrate via a number of methods including, but not limited to adhesives or conformal contact.

Figure 36A:
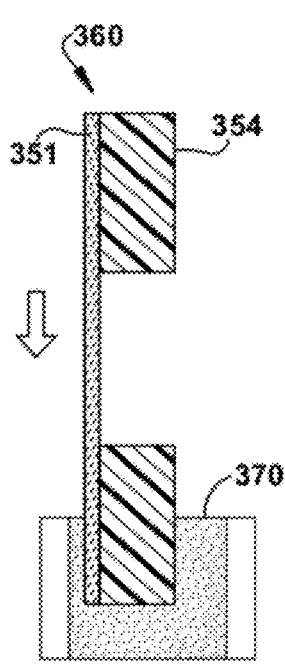
FIGS. 36a-36c illustrate an exemplary embodiment of the present invention being inserted and removed from a liquid sample.
Figure 36B:
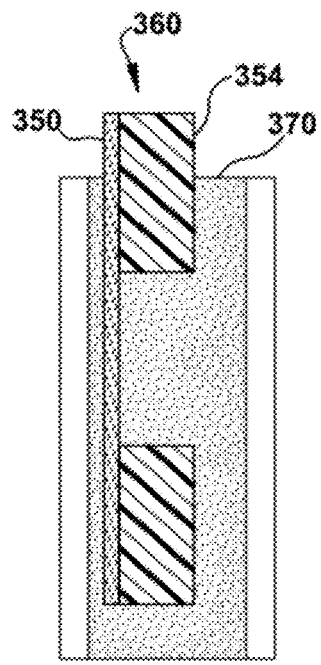
Figure 36C:
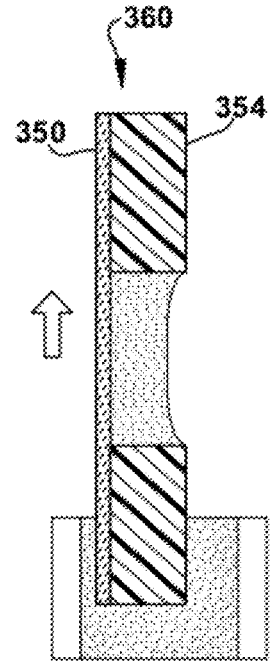

As best shown in FIGS. 36a-c, when the device 360 is inserted into a liquid sample 370, the sample enters the reservoirs in the mask 354. Upon removal of the sample container, surface tension of the reservoir walls results in the isolation of discreet volumes 372 of sample in the mask reservoirs. Factors that impact the uniformity of sample delivery include reservoir diameter, reservoir depth, mask surface energy and mask withdrawal rate.

EXAMPLE 13

Figure 37:
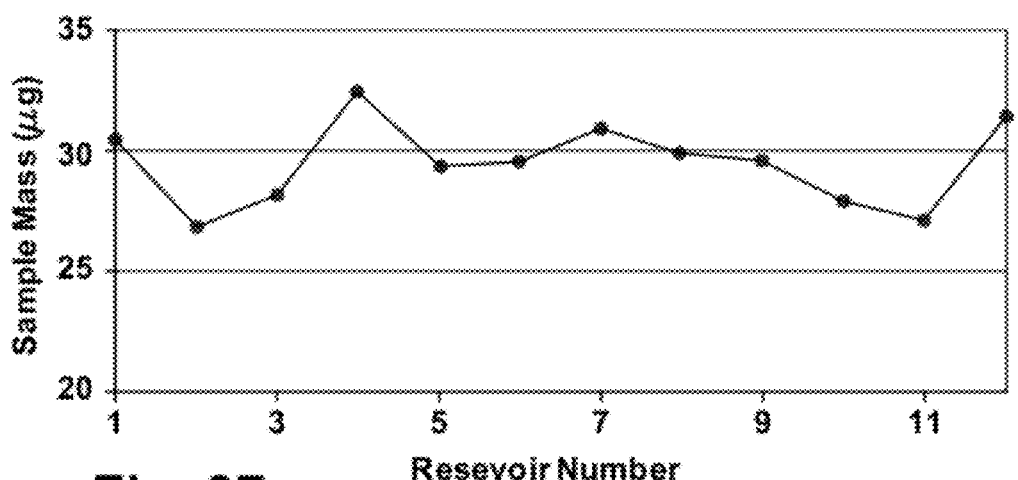
FIG. 37 is a graph illustrating the performance of an exemplary delivery device constructed in accordance with FIGS. 34a-34b.

FIG. 37 illustrates the performance of a sample delivery device configured in accordance with FIGS. 34a-b. In this Example 13, the substrate 350 was made of polycarbonate while the reservoir mask 354 was produced from a 1.5 mm thick sheet of polydimethylsiloxane (PDMS). Reservoirs 352 were punched in the PDMS mask such that 5 mm diameter holes were produced. The substrate 350 with attached mask 354 was vertically dipped into a vessel containing deionized water and then rapidly withdrawn (~2.5 cm/s). Water isolated in individual reservoirs was quantified with an analytical balance. In the described configuration, the delivered sample mass was 29.4+/−1.7 µg, resulting in a reservoir-to-reservoir reproducibility of 5.7%.

In other exemplary embodiments, it is understood that the reservoir mask 354 can be modified to incorporate both hydrophobic and hydrophilic functionalities. In the embodiment of Example 13, one of the potential causes of degraded sample mass reproducibility was identified as addition of isolated sample droplets initially located on the hydrophobic mask between reservoirs to the sample mass located in a reservoir. To minimize this phenomenon, portions of the reservoir mask can be modified to impart hydrophilic characteristics. As shown in FIGS. 35a, 35b, this modification can be generated by the addition of a thin hydrophilic film 380 to the reservoir mask or the surface modification of the reservoir mask itself through coatings on treatment (UV or plasma). Sample volume isolation occurs by maintaining a hydrophobic region immediately surrounding the individual reservoirs. Droplets initially located between the individual reservoirs coalesce on the hydrophilic regions of the mask and are removed by gravity.

EXAMPLE 14

Figure 38:
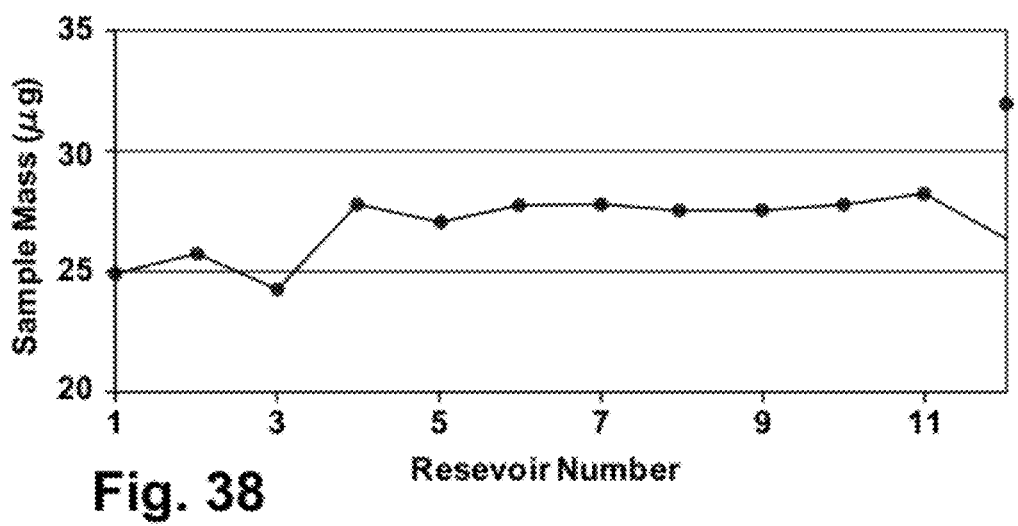
FIG. 38 is a graph illustrating the performance of an exemplary delivery device constructed in accordance with FIGS. 35a-35b.

FIG. 38 illustrates the performance of a sample delivery device configured in accordance with FIGS. 35a-b. In this Example 14, the substrate 350 was made of polycarbonate while the reservoir mask 354 was produced from a 1.5 mm thick sheet of PDMS. Reservoirs 352 were punched in the PDMS mask such that 5 mm diameter holes were produced. The reservoirs were temporarily covered with 9 mm diameter pieces of tape to allow for surface modification. The PDMS was modified with an air plasma to produce a hydrophilic surface in exposed areas. The tape was then removed to produce a multi-functional surface. The substrate with attached mask was vertically dipped into a vessel containing deionized water and then rapidly withdrawn (~2.5 cm/s). Water isolated in individual reservoirs was quantified with an analytical balance. In the described configuration, the delivered sample mass was 27.0+/−1.2 μg, resulting in a reservoir-to-reservoir reproducibility of 4.6%.

While the disclosure has been illustrated and described in typical exemplary embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the scope of the disclosure as defined by the following claims.

What is claimed is:

1. A system for simultaneously measuring a plurality of biological or chemical analytes in a fluid, said system comprising:
    a substrate comprising a plurality of sensor elements, each said sensor element responding to at least one of said plurality of analytes;
    at least one light source for directing light onto said sensor elements;
    a detector means for detecting a response from said sensor elements, wherein said detector means includes a processor that is programmed to:
        convert said response from each of said sensor elements into a digital record;
        execute an image identification algorithm for identifying said at least one analyte based on said digital record, wherein an analyte identification output is produced for each of said at least one analyte identified; and
        execute an optimization algorithm for identifying a concentration for each of said at least one analyte, wherein a concentration output is produced for each analyte identification output; and
    a delivery means for delivering metered quantities of said fluid to each said sensor element, wherein said delivery means comprises a delivery device comprising a plurality of reservoirs communicating with said sensor elements, said delivery device further comprising a sample entry port and a plurality of hydrophilic fluidic channels, said channels being connected between said reservoirs and said entry port so as to transport a controlled volume of said fluid between said entry port and said reservoirs, said delivery device further comprising a cover layer attached to said delivery device, said cover layer comprising a plurality of substantially hydrophobic vent holes disposed above said reservoirs, said cover layer further comprising a substantially hydrophilic bottom surface for providing a hydrophilic roof portion above said reservoirs to facilitate transport of said fluid to said reservoirs.

2. The system of claim 1, wherein said sensor elements are disposed within said reservoirs or on a bottom surface of said cover layer.

3. The system of claim 1, wherein said delivery device permanently adheres to said substrate.

4. The system of claim 1, wherein said delivery device detachably adheres to said substrate.

5. The system of claim 1, wherein said delivery device further comprises an o-ring operatively associated with said entry port, said o-ring being adapted to absorb excess fluid that spills over the top of said delivery device.

6. The system of claim 1, wherein said substrate is a DVD, CD, double-layer, or blu-ray disk.

7. The system of claim 6, further comprising an optical drive for quantifying said response, wherein said delivery means comprises a disk case for enclosing said substrate.

8. The system of claim 7, further comprising a blotting layer to remove excess fluid from said substrate.

9. The system of claim 1, wherein said channels are capillary channels adapted to transport said metered quantities of said fluid from said entry port to said reservoirs by capillary force without the use of wicking materials or pumps.

10. The system of claim 1, wherein said delivery means comprises means for delivering said fluid to said sensor elements by way of electro-osmotic flow, electro-wetting, thermo-capillary pumping, magnetic fields, surface directed flow, electro-chemical control, mechanical devices, centripetal force, surface energy gradients, or combinations thereof.

* * * * *